United States Patent
Scarabelli et al.

(10) Patent No.: US 12,005,448 B2
(45) Date of Patent: Jun. 11, 2024

(54) SYSTEMS AND METHODS OF USING ANISOTROPIC NANOSTRUCTURES IN MICROFLUIDIC DEVICES FOR BINDING AND OPTIONAL RELEASE OF MOLECULES AND CELLS

(71) Applicant: THE REGENTS OF THE UNIVERSITY OF CALIFORNIA, Oakland, CA (US)

(72) Inventors: Leonardo Scarabelli, Los Angeles, CA (US); Gail Vinnacombe, Los Angeles, CA (US); Liv Heidenreich, Los Angeles, CA (US); Naihao Chiang, Los Angeles, CA (US); Yao Gong, Los Angeles, CA (US); Paul S. Weiss, Los Angeles, CA (US); Steven J. Jonas, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 657 days.

(21) Appl. No.: 17/268,955

(22) PCT Filed: Aug. 16, 2019

(86) PCT No.: PCT/US2019/046874
§ 371 (c)(1),
(2) Date: Feb. 16, 2021

(87) PCT Pub. No.: WO2020/037238
PCT Pub. Date: Feb. 20, 2020

(65) Prior Publication Data
US 2021/0308671 A1    Oct. 7, 2021

Related U.S. Application Data

(60) Provisional application No. 62/719,505, filed on Aug. 17, 2018.

(51) Int. Cl.
*B01L 3/00* (2006.01)
*C01G 7/00* (2006.01)
(Continued)

(52) U.S. Cl.
CPC ..... *B01L 3/50273* (2013.01); *B01L 3/502761* (2013.01); *C01G 7/00* (2013.01);
(Continued)

(58) Field of Classification Search
CPC ..... B01L 2300/0838; B01L 2300/0896; B01L 2300/168; B01L 2400/0478;
(Continued)

(56) References Cited

U.S. PATENT DOCUMENTS

2008/0278728 A1    11/2008    Tetz et al.
2011/0122406 A1    5/2011     Khine et al.
(Continued)

FOREIGN PATENT DOCUMENTS

WO    WO 2018/148715    8/2018
WO    WO 2019/060989    4/2019

OTHER PUBLICATIONS

Pallavicini, P. et al., Synthesis of branched Au nanoparticles with tunable near-infrared LSPR using a zwitterionic surfactant, Chem. Commun., 2011, 47, 1315-1317, 1315.
(Continued)

*Primary Examiner* — Jennifer Wecker
(74) *Attorney, Agent, or Firm* — VISTA IP LAW GROUP LLP

(57) ABSTRACT

Systems and methods are disclosed that utilize metal nanostructures that are synthesized in situ along the internal surfaces of a microfluidic device. The nanostructures are formed by initial deposition of metallic seeds followed by flowing growth and reducing agent solutions into the capillaries/microfluidic channels to grow the nanostars. The
(Continued)

nanostructures may optionally be functionalized with a capture ligand. The capture ligand may be used to selectively bind to certain cells (e.g., circulating tumor cells). The cells may be removed by a beam of light (e.g., laser beam) that induces localized heating at the surface location(s) containing the nanostructures. The plasmonic nature of the nanostructures can be used to heat the nanostructure(s) locally for the selective removal of one or certain cells. The nanostructures may be used to acquire Raman spectra of molecules or other small objects that are bound thereto for identification and quantification.

14 Claims, 13 Drawing Sheets

(51) Int. Cl.
| | | |
|---|---|---|
| G01N 21/64 | (2006.01) | |
| G01N 21/65 | (2006.01) | |
| G01N 33/543 | (2006.01) | |
| G01N 33/574 | (2006.01) | |
| G02B 21/00 | (2006.01) | |
| G02B 21/16 | (2006.01) | |
| B82Y 35/00 | (2011.01) | |

(52) U.S. Cl.
CPC ....... *G01N 21/6458* (2013.01); *G01N 21/658* (2013.01); *G01N 33/54346* (2013.01); *G01N 33/57492* (2013.01); *G02B 21/006* (2013.01); *G02B 21/16* (2013.01); *B01L 2300/0838* (2013.01); *B01L 2300/0896* (2013.01); *B01L 2400/0478* (2013.01); *B82Y 35/00* (2013.01); *C01P 2004/03* (2013.01); *C01P 2004/30* (2013.01); *C01P 2004/64* (2013.01); *G01N 2021/656* (2013.01)

(58) Field of Classification Search
CPC ........... B01L 3/502707; B01L 3/50273; B01L 3/502761; C01G 7/00; B82Y 35/00; C12N 5/0693; G01N 2021/656; G01N 21/6458; G01N 21/658; G01N 33/54346; G01N 33/57492; G02B 21/006; G02B 21/16; C01P 2004/03; C01P 2004/30; C01P 2004/64

See application file for complete search history.

(56) References Cited

U.S. PATENT DOCUMENTS

| | | | | |
|---|---|---|---|---|
| 2012/0262718 | A1* | 10/2012 | Yamada | G01N 21/55 356/436 |
| 2014/0106469 | A1 | 4/2014 | Wu et al. | |
| 2015/0253321 | A1* | 9/2015 | Chou | G01N 33/54386 435/7.1 |
| 2016/0018331 | A1 | 1/2016 | Blair et al. | |
| 2016/0355869 | A1* | 12/2016 | Blair | G01N 21/648 |
| 2017/0151331 | A1* | 6/2017 | Vo-Dinh | A61K 41/0052 |
| 2018/0202903 | A1* | 7/2018 | Chou | G01N 33/54366 |
| 2018/0348175 | A1* | 12/2018 | Auner | G01N 30/6091 |

OTHER PUBLICATIONS

Jeanmaire, David L. et al., Surface Raman Spectroelectrochemistry, Part I. Heterocyclic, Aromatic, and Alphatic Amines Adsorbed on the Anodized Silver Electrode, J. Electroanal. Chem., 84 (1977) 1-20.

Casu, Alberto et al., Controlled Synthesis of Gold Nanostars by Using a Zwitterionic Surfactant, Chem. Eur. J. 2012, 18, 9381-9390.

Scarabelli, Leonardo, Recent advances in the rational synthesis and self-assembly of anisotropic plasmonic nanoparticles, Pure Appl. Chem. 2018; 90(9): 1393-1407.

PCT International Search Report and Written Opinion for PCT/US2019/046874, Applicant: The Regents of the University of California, dated Dec. 18, 2019 (14 pages).

Claridge, Shelley A. et al., From the Bottom Up: Dimensional Control and Characterization in Molecular Monolayers, Chem Soc Rev. Apr. 7, 2013; 42(7): 2725-2745. doi:10.1039/c2cs35365b.

Giner-Casares, Juan J. et al., Plasmonic Surfaces for Cell Growth and Retrieval Triggered by Near-Infrared Light, Angew. Chem. Int. Ed. 2016, 55, 974-978.

Hao, Feng et al., Plasmon Resonances of a Gold Nanostar, Nano Lett., vol. 7, No. 3, 2007.

He, Jiating et al., Forest of Gold Nanowires: A New Type of Nanocrystal Growth, ACSNano, vol. 7, No. 3, 2733-2740, 2013.

Hou, Shuang, Capture and Stimulated Release of Circulating Tumor Cells on Polymer Grafted Silicon Nanostructures, Adv Mater. Mar. 20, 2013; 25(11): 1547-1551. doi:10.1002/adma.201203185.

Hou, Shuang, Polymer Nanofiber-Embedded Microchips for Detection, Isolation, and Molecular Analysis of Single Circulating, Melanoma Cells, Angew Chem Int Ed Engl. Mar. 18, 2013; 52(12): . doi:10.1002/anie.201208452.

Lin, Millicent et al., Nanovelcro Cell-Affinity Assay for Detecting and Characterizing Circulating Tumor Cells, DOI: 10.1002/9781119244554.ch9; https://www.researchgate.net/publication/299645568, Apr. 2016.

Lohse, Samuel E., et al., Anisotropic Noble Metal Nanocrystal Growth: The Role of Halides, Chem. Mater. 2014, 26, 34-43, dx.doi.org/10.1021/cm402384j.

Love, Christoper J., et al., Self-Assembled Monolayers of Thiolates on Metals as a Form of Nanotechnology, Chem. Rev. 2005, 105, 1103-1169.

Lv, Song-Wei, et al., Near-Infrared Light-Responsive Hydrogel for Specific Recognition and Photothermal Site-Release of Circulating Tumor Cells, ACS Nano 2016, 10, 6201-6210, DOI: 10.1021/acsnano.6b02208.

Pallavicini, Piersandro et al., Self-assembled monolayers of gold nanostars: a convenient tool for near-IR photothermal biofilm eradication, Chem. Commun., 2014, 50, 1969.

Stranick, S.J. et al., A New Mechanism for Surface Diffusion: Motion of a Substrate-Adsorbate Complex, J. Phys. Chem, 1994, 98, 11135-11142.

Wang, Shutao, Highly Efficient Capture of Circulating Tumor Cells Using Nanostructured Silicon Substrates with Integrated Chaotic Micromixers, Angew Chem Int Ed Engl. Mar. 21, 2011; 50(13): 3084-3088. doi:10.1002/anie.201005853.

Weiss, Paul, Functional Molecules and Assemblies in Controlled Environments: Formation and Measurements, Accounts of Chemical Research, 1772-1781, Dec. 2008 vol. 41, No. 12.

Zrimsek, Alyssa B. et al., Single-Molecule Chemistry with Surface- and Tip-Enhanced Raman Spectroscopy, Chem. Rev. 2017,117,7583-7613, DOI: 10.1021/acs.chemrev.6b00552.

* cited by examiner

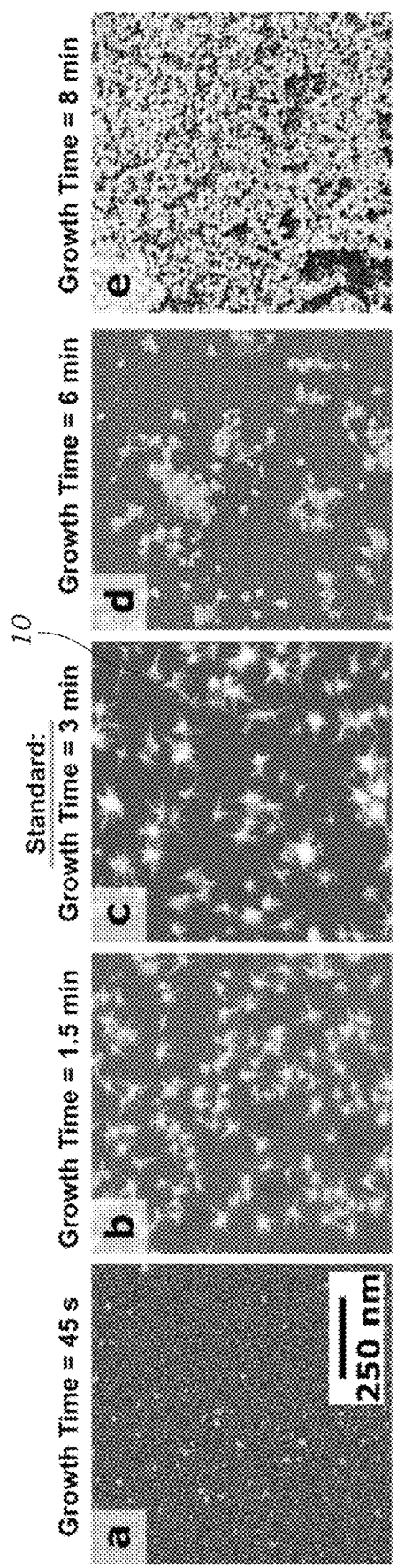
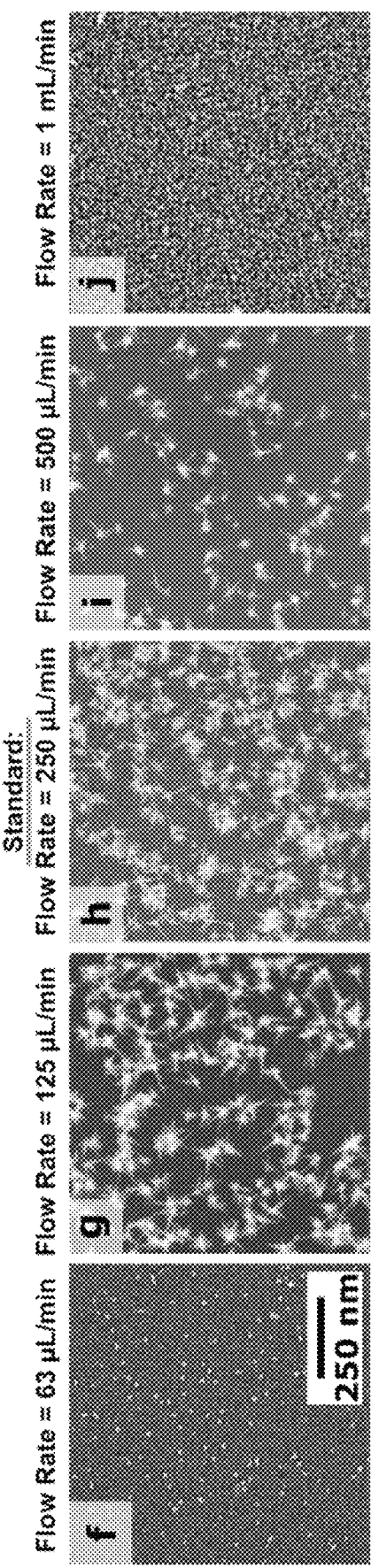

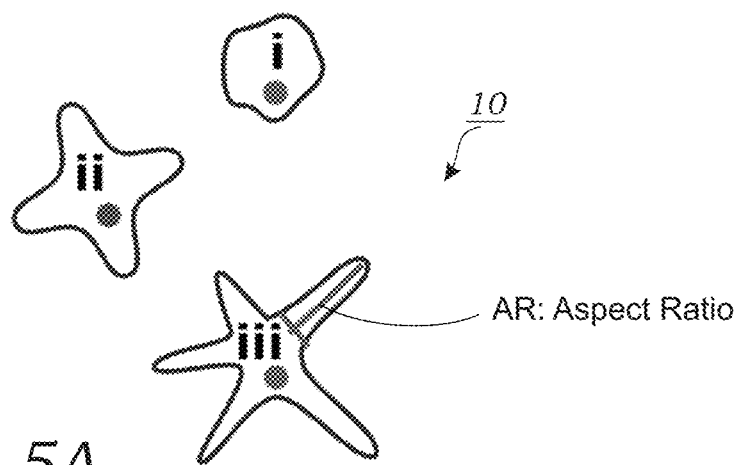
FIG. 5A
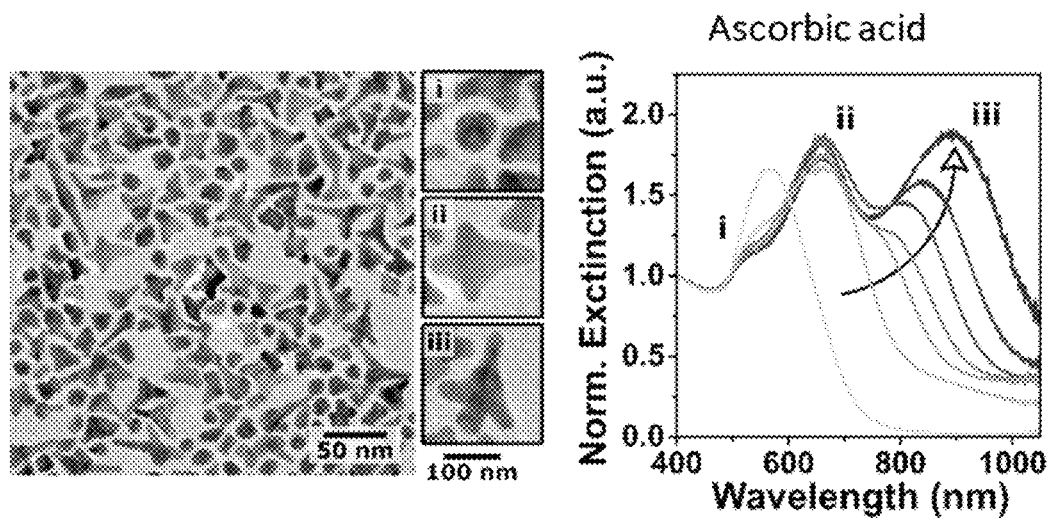
FIG. 5B
FIG. 5C
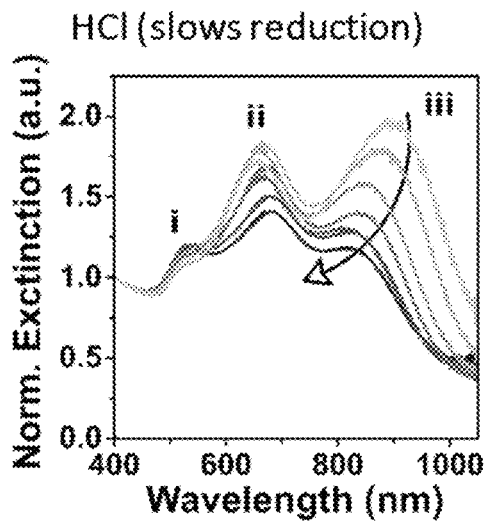
FIG. 5D
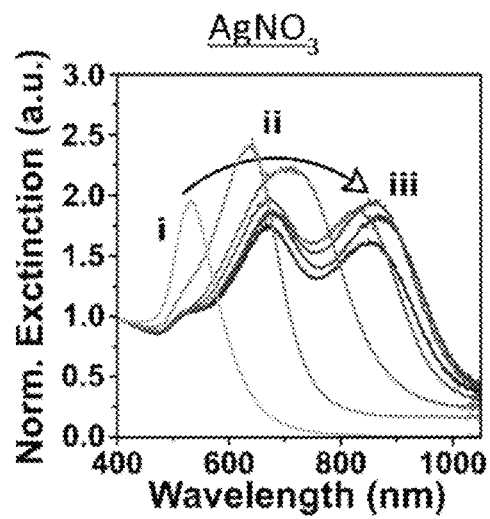
FIG. 5E

SYSTEMS AND METHODS OF USING ANISOTROPIC NANOSTRUCTURES IN MICROFLUIDIC DEVICES FOR BINDING AND OPTIONAL RELEASE OF MOLECULES AND CELLS

RELATED APPLICATION

This Application is a U.S. National Stage filing under 35 U.S.C. § 371 of International Application No. PCT/US2019/046874, filed Aug. 16, 2019, which claims priority to U.S. Provisional Patent Application No. 62/719,505 filed on Aug. 17, 2018, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with government support under DA045550, awarded by the National Institutes of Health. The government has certain rights in the invention.

TECHNICAL FIELD

The technical field generally relates to the utilization of nanostructures in microfluidic-based devices that exhibit plasmonic activity or a plasmonic response in one or more selected regions of the electromagnetic spectrum. In particular, the technical field of the invention relates to the use of metallic nanostars that are synthesized in situ along the internal walls of the microfluidic device.

BACKGROUND

The development of new diagnostic tools capable of detecting cancer in its early stages, recognizing different molecular subtypes, monitoring disease evolution, and ultimately identifying the best treatment strategy for individual patients represents the next step towards personalized anti-cancer treatment. There is emerging interest in utilizing circulating tumor cells (CTCs) as "liquid biopsy" samples to provide real-time information for characterizing the disease status of cancer patients. However, due to their extremely low abundance in peripheral blood, CTCs from pediatric cancers are difficult to detect using existing technologies. Existing technologies for obtaining CTCs leverage magnetic bead-based sorting, nanostructured interfaces, or microfluidic vortexes to capture CTCs selectively from patient-derived samples. However, these strategies fall short in their ability to release captured cells for further analysis or in capturing non-epithelial derived malignancies (e.g., sarcomas, neuroblastoma, brain tumors). Similarly, selective cell capture technologies have potentially powerful applications in maternal-fetal medicine for prenatal diagnosis of genetic disorders and/or monitoring maternal and/or fetal health during gestation.

Current clinical laboratory improvement amendment (CLIA)-certified reference methods used to quantify concentrations of drugs used in the management of cancer, solid organ transplant, infectious diseases, and others are typically based on mass spectrometry, chromatographic, and/or immunoenzymatic-based assays (e.g., enzyme linked immunoassays, ELISA). While these methods are widely used by clinical laboratories to provide critical diagnostic information (e.g., drug concentration, activity, etc.) to physicians, this information is typically not available in real time nor are these methods easily adapted for point-of-care applications. The effective monitoring of immunosuppressive medications represents a particular challenge for streamlining the care of patients who have received solid organ or hematopoietic stem cell transplants or who are undergoing treatment for autoimmune diseases and other related pathologies.

Other methods, such as one reported by Menotta et al., Label-free quantification of Tacrolimus in biological samples by atomic force microscopy, *Anal. Chim. Acta,* 884, 90-96 (2015) attempt to leverage atomic force microscopy (AFM) for the quantitative analysis of FK506 (Tacrolimus) in whole blood (WB) samples. This AFM-based biosensor utilizes a capture ligand, the endogen drug receptor FKBP12, to quantify Tacrolimus levels. The biosensor was first assayed to detect the free drug in solution, and subsequently used for the detection of Tacrolimus in blood samples. The sensor was suitable to generate a dose-response curve in the full range of clinical drug monitoring but is labor intensive and not capable of real-time detection. The methods and devices described herein have much broader applicability, sensitivity, and utility.

SUMMARY

In one embodiment, a microfluidic-based system is disclosed that forms plasmonic nanostructures on the internal surfaces of a microfluidic device. The plasmonic nanostructures, in one preferred embodiment, include nanostars and in particular gold nanostars. The plasmonic nanostructures may be formed on the inner surface of a microfluidic channel (e.g., microchannel), capillary, chamber, well, or other regions of a microfluidic device. As explained herein, the plasmonic nanostructures are grown in situ on the internal flow surfaces of the microfluidic device. In some embodiments, the internal flow surfaces include a plurality of microfluidic channels or capillaries populated with plasmonic nanostructures that are used to increase device throughput. In one embodiment, the nanostructures display plasmonic activity in the near-infrared or other selected regions of the electromagnetic spectrum. The materials (e.g., gold in one embodiment), shape, and size determine the plasmonic resonance energy. The nanostructures present at these surfaces are assembled within the internal flow surface(s) of the microfluidic device (e.g., microfluidic capillaries or microfluidic channels) to enable sensing of clinically relevant biomolecules and/or capturing cells or other biomolecular assemblies. The microfluidic device may be made from glass, silica, and/or silicon, and other oxide-containing substrates, or from any number of polymer materials. Flow through the microfluidic device is controlled such as by connecting the flow paths within the microfluidic device (e.g., microfluidic channels or capillaries) to a computer-controlled pump such as a syringe pump.

In one particular embodiment, the surface chemistry of the plasmonic nanostructures is modified to capture cells and/or molecules (e.g., biomolecules). For example, the surfaces of the gold nanostars may be functionalized with one or more capture ligands, which may be an antibody, aptamer, protein or other binding molecule. For example, the antibody, aptamer (or other binding molecule) may be specific for capturing CTCs on the surface(s) of the microfluidic device populated with the gold nanostars. In another embodiment, the antibody, aptamer (or other bonding molecule) may be specific for capturing one or more molecules, which may include biomolecules, drugs, metabolites, analytes, etc. In some embodiments, the cells that are captured on the inner surface of the microfluidic device may be selectively released via hyperthermia-mediated cell detachment. For example, localized heating at specific regions of the microfluidic device containing the trapped cells or even on a specific nanostructure may be used to release the cell or cells from the surface which can then flow downstream for capture and/or analysis. In one particular method, a beam of light (e.g., a laser) is used to create the localized heating to release cells from the surface of the nanostructures within the microfluidic device. The illuminated plasmonic nanostructure can be used to generate and to localize the heat.

In another embodiment, the trapped cells or molecules (e.g., biomolecules) are subject to Raman interrogation, scanning, or imaging such as by a Raman spectrometer or Raman microscope. This may also include using surface-enhanced Raman spectroscopy (SERS). The SERS technique is a chemical fingerprint method that uses measured Raman spectra that appear as "peaks" due to molecular vibrations and are thus characteristic of the functional groups in the molecule(s) and thus its (their) identity. The acquired Raman spectra have peak locations and intensities that are compared to corresponding reference Raman spectra, which contain peak locations and intensities that are unique to the molecule(s) and/or cell(s) of interest. If the peak locations and relative intensities match the reference peak locations and relative intensities within a predefined margin of error, the target molecule (or cell) is confirmed to be present in the sample. Similarly, the concentrations of the molecule(s) or cell(s) can be determined by whether the peak intensities match the reference peak intensities within a predefined margin of error.

The systems and methods described herein satisfy specific unmet needs identified in areas relating to the selective detection and release of CTCs and other rare cells for monitoring the progression of aggressive malignancies as well as the real-time monitoring clinically-relevant biomarker and/or drugs in a point-of-care format. In particular, the efficient isolation of CTCs via this approach will enable applications relevant to clinical oncology in strategies for disease monitoring and the optimization of current and future therapeutic regimens. Conventional strategies for disease monitoring and surveillance rely on serial radiographic imaging studies that often detect the spread of the disease too late for effective treatment and are limited by the sensitivity and resolution of the imaging modality used. The disclosed platform and methods address these limitations by enabling the early detection of cells with the most metastatic potential, enhancing disease monitoring and opening new avenues for the development of patient-specific therapeutic strategies. The real-time monitoring of biomarkers and/or clinically-relevant compounds using simple, cost-effective materials enables new capabilities for the design and application of portable devices capable of screening, monitoring, and verifying the efficacy of medical interventions, including for personalized medicine approaches.

The systems and methods described herein use metal nanostructures (e.g., gold nanostars) that are synthesized in situ along the internal surface(s) of the microfluidic device that, in one embodiment, are used to selectively capture and optionally to release cells such as CTCs. The seed-mediated approach for the growth of anisotropic plasmonic materials has been the subject of extensive research, with particular attention dedicated to the control of the nanoparticle morphology, which is directly linked to their optical properties. However, less attention has been dedicated to the possibility of growing anisotropic structures directly on substrates. The approach disclosed herein takes advantage of in situ growth that is coupled to microfluidic systems to direct synthesis. The morphology and surface density of the nanostructures is important for CTC capture. For example, nanowires would not be comparable in this regard, being more fragile and presenting less intense plasmonic activity in the wavelength region of interest. The near-infrared is typically desirable as certain bands in this wavelength range minimize damage to biomolecules, biomaterials, and cells. The visible and ultraviolet regions can also be used by the appropriate selection of materials and nanostructures.

Plasmons or nanostructures that exhibit plasmonic properties can be exploited for the enhancement of weak optical signals, such as Raman scattering. In the last decade, the sensing capabilities of SERS have been pushed to the limit of single-molecule detection. In order to combine this sensing capability with microfluidics, the possibility of growing plasmonic nanostructures in situ inside the fluid contacting surfaces of a microfluidic device is essential. The approach described herein provides a robust way of fabricating such nanostructures directly in flow contacting surfaces, enabling the coverage of the entire available surface, and at the same time avoiding problems such as device sealing and leakage.

In one embodiment, a microfluidic device (e.g., substrate or chip) contains one or more microfluidic channels or capillaries having one or more inner surfaces populated with a plurality of metal anisotropic nanostructures disposed thereon, wherein the metal anisotropic nanostructures exhibit plasmonic activity in one or more wavelength ranges. In one preferred aspect, the metal anisotropic nanostructures are gold nanostars which exhibit plasmonic activity in the near-infrared region of the electromagnetic spectrum. The metal anisotropic nanostructures may further be functionalized with a capture ligand that is used to capture a cell or molecules. In some embodiments, illumination (e.g., via a laser) is provided to selectively release trapped cells by localized heating of the surface containing the adhered cells. The illumination can be local to release one or a few cells, or it can be broad or rastered to release cells in the illuminated area.

In one embodiment, a system including the microfluidic device described above may further include a SERS spectrometer configured to measure Raman spectra of one or more target molecules, compounds, or materials disposed on the inner surface of the one or more microfluidic channels or capillaries. A computing device associated or communicating with the SERS spectrometer contains software executed thereon that identifies the molecules based on the Raman spectra obtained by the SERS spectrometer.

In another embodiment, a system including the microfluidic device described above may further include an optical microscope configured to image cells disposed on the inner surface of the one or more microfluidic channels or capillaries. The system further includes a laser configured to illuminate the inner surface of the one or more microfluidic channels or capillaries for localized heating to release adhered cells. The optical microscope may include fluorescence, Raman, and/or confocal capabilities.

In one embodiment, a method of capturing and releasing cells of a particular type contained in a sample includes providing a microfluidic device comprising one or more microfluidic channels or capillaries having one or more inner surfaces populated with a plurality of metal anisotropic nanostructures disposed thereon and functionalized with a capture ligand to a specific cell type, wherein the metal anisotropic nanostructures exhibit plasmonic activity in a near-infrared wavelength range. A sample containing the cells is flowed through the one or more microfluidic channels or capillaries, wherein the cells of the particular type are adhered to the one or more inner surfaces. The microfluidic device is then optically interrogated with an optical microscope to locate the adhered cells. The adhered cells are then released from the one or more inner surfaces by application of laser light onto the one or more inner surfaces where the adhered cells are located.

In another embodiment, a method of forming a plurality of anisotropic nanostructures in one or more microfluidic channels or capillaries includes the operations of functionalizing an inner surface of the one or more microfluidic channels or capillaries with a chemical coupling agent and depositing metal seed particles on the functionalized inner surface. A metal-containing growth solution mixed with a reducing agent is then flowed into the one or more microfluidic channels or capillaries to grow the plurality of anisotropic nanostructures disposed on the inner surface of the one or more microfluidic channels or capillaries. In one particular embodiment, the seeds are cetyltrimethylammonium chloride (CTAC)-coated gold seeds and the metal-containing growth solution comprises gold(III) chloride, silver nitrate, and hydrochloric acid, and N-dodecyl-N,N-dimethyl-3-ammonio-1-propanesulfonate (LSB) and the reducing agent comprises ascorbic acid.

BRIEF DESCRIPTION OF THE DRAWINGS

FIGS. 4A-4E illustrate scanning electron micrographs of a capillary having grown gold nanostars showing the effect of growth time.

FIGS. 4F-4J illustrate scanning electron micrographs of a capillary having grown gold nanostars showing the effect of flow rate.

FIG. 5A illustrates different types of major products yielded by the growth of gold nanostars in solution (colloidal). These include anisotropic spheroids (i), low-aspect ratio nanostars (ii), and high-aspect ratio nanostars (iii). The in situ growth methods were optimized to produce high-aspect ratio nanostars (iii).

FIG. 5B illustrates a micrograph image of the different products yielded by the growth of gold nanostars in solution including anisotropic spheroids (i), low-aspect ratio nanostars (ii), and high-aspect ratio nanostars (iii).

FIG. 5C illustrates the ultraviolet-visible spectra of gold nanostar synthesized with varying concentrations of hydrochloric acid, where (i) anisotropic spheroids, (ii) low aspect-ratio gold nanostars, and (iii) high aspect-ratio gold nanostars, correspond to the peaks at about 500 nm, about 650 nm, and about 875 nm, respectively. The arrow shows the trend of increasing HCL concentration.

FIG. 5D illustrates the ultraviolet-visible spectra of gold nanostar synthesized with varying concentrations of ascorbic acid, where (i) anisotropic spheroids, (ii) low aspect-ratio gold nanostars, and (iii) high aspect-ratio gold nanostars, correspond to the peaks at about 500 nm, about 650 nm, and about. 875 nm, respectively. The arrow shows the trend of increasing ascorbic acid concentration.

FIG. 5E illustrates the ultraviolet-visible spectra of gold nanostar synthesized with varying concentrations of silver cations, where (i) anisotropic spheroids, (ii) low aspect-ratio gold nanostars, and (iii) high aspect-ratio gold nanostars, correspond to the peaks at about 500 nm, about 650 nm, and about. 875 nm, respectively. The arrow shows the trend of increasing ascorbic acid concentration.

FIG. 11B illustrates an enlarged view of the rectangular region of FIG. 11A.

DETAILED DESCRIPTION OF THE ILLUSTRATED EMBODIMENTS

Figure 1:
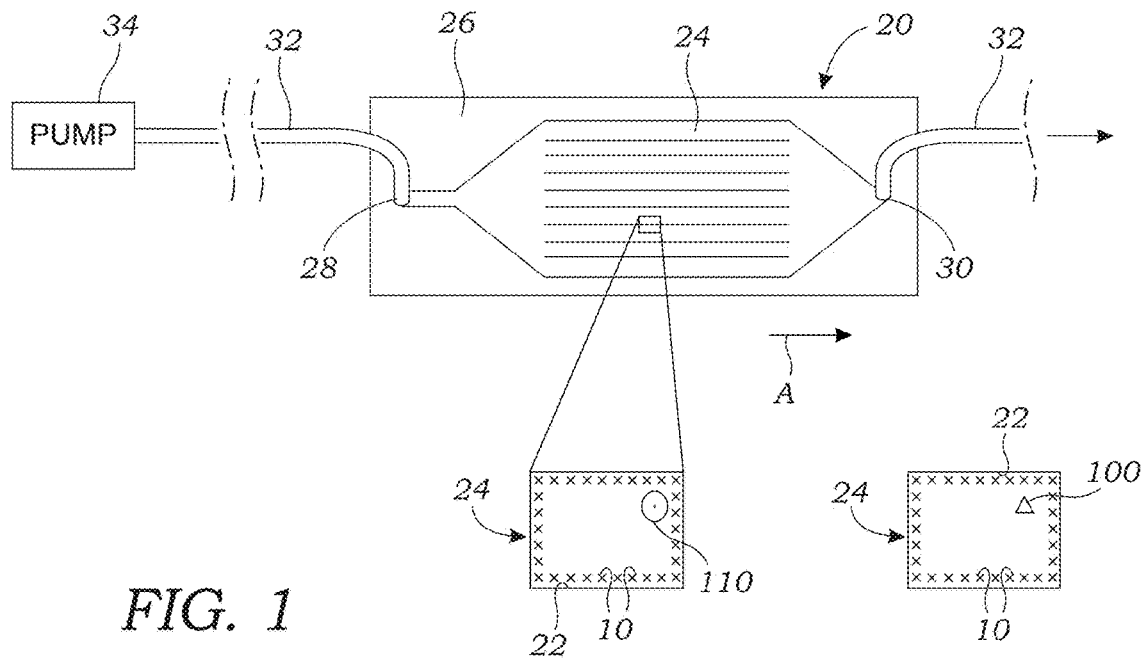
FIG. 1 schematically illustrates a microfluidic system that includes one or more microfluidic channels or capillaries formed in a substrate or chip. The microfluidic channels or capillaries are populated with nanostructures that are functionalized to capture either cells or molecules (e.g., biomolecules).
Figure 2A:
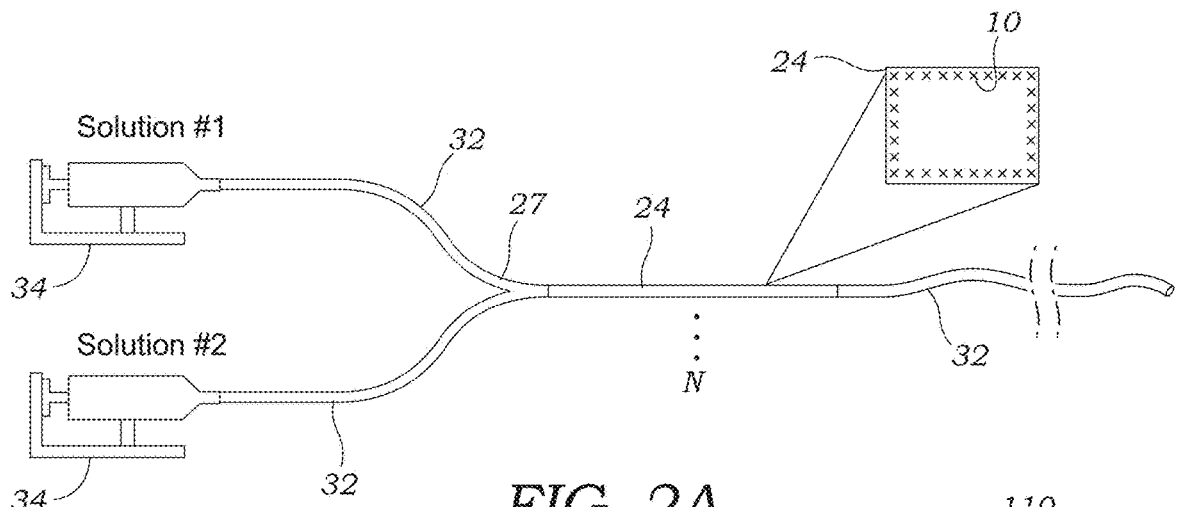
FIG. 2A illustrates a single capillary or microfluidic channel in which nanostars (e.g., gold nanostars) are grown in situ on internal surfaces thereof. In this embodiment, two separate pumps are used to flow separate solutions into the single capillary or microfluidic channel using a Y-split. Alternatively, the two solutions may be mixed immediately prior to passing through the one or more microfluidic channels or capillaries like the embodiment of FIG. 2B.
Figure 2B:
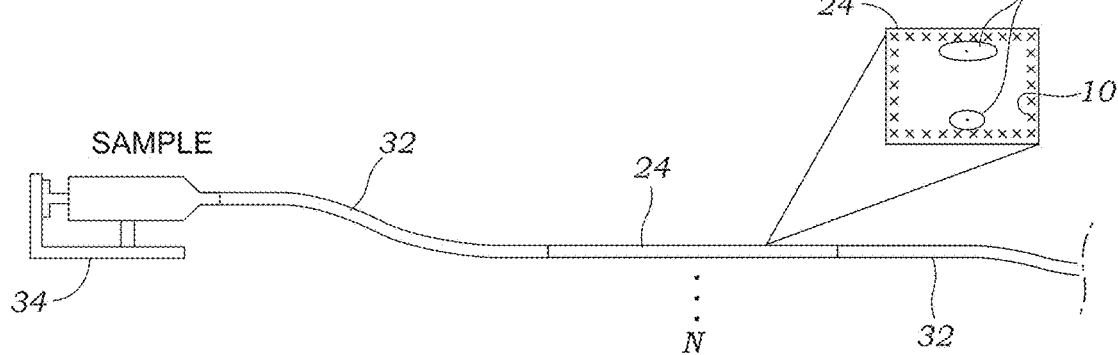
FIG. 2B illustrates a sample fluid (containing cells or molecules) being flowed through a single capillary or microfluidic channel that has nanostars disposed on internal surfaces thereof. The cross-sectional view illustrates cells that have adhered to functionalized nanostars (e.g., with an antibody functionalized on the nanostars).

Systems and methods are described herein that integrate microfluidic technologies combined with nanostructured interfaces (i.e., nanostructures 10) that display plasmonic activity in the near-infrared or other selected regions of the electromagnetic spectrum. With reference to FIG. 1, the nanostructures 10 are anisotropic plasmonic structures present on the fluid-contacting surface(s) 22 of a microfluidic device 20. In one particular embodiment, the nanostructures 10 are highly branched, anisotropic nanostars. The fluid-contacting surface(s) 22 of the microfluidic device 20 may include the inner surface(s) of a microfluidic channel, capillary, well, chamber, or the like of the microfluidic device 20. In one particular embodiment, the nanostructures 10 are formed on the inner surfaces 22 of one or more microfluidic channels or one or more capillaries 24 present within the microfluidic device 20. As seen in FIG. 1, the microfluidic channels or capillaries 24 are formed in a substrate or chip 26 that includes an inlet 28 and an outlet 30. Fluid flows in the direction of arrow A from the inlet 28 and into the microfluidic channels or capillaries 24 and leaves the microfluidic device 20 via the outlet 30. Tubing 32 may be connected to both the inlet 28 and the outlet 30 as illustrated in FIGS. 1, 2A, 2B. One or more pumps 34 are connected to the tubing 32 connected to the inlet 28. The one or more pumps 34 are used to pump fluids (e.g., sample) and reagents to form the nanostructures 10 as described herein. The one or more pumps 34 are also used after formation of the nanostructures 10 to run a sample fluid through the microfluidic device 20.

The nanostructures 10 are assembled in situ within the fluid-contacting surface(s) 22 to enable sensing of clinically relevant biomolecules 100 and/or capturing cells 110 or other biomolecular assemblies (seen in FIGS. 1, 2B, 8A, 8B, 9, and 12). In one embodiment, the nanostructures 10 are formed as gold nanostars (FIGS. 5A and 5B (iii)) which include a number of protuberances or spikes that extend generally outward from a central region of the nanostructure 10. The protuberances or spikes form a particle that has a high aspect ratio. For example, gold nanostars 10 formed on the fluid-contacting surface 22 of a microfluidic channel or capillary 24 may have a core size (core excludes protuberances or spikes) of around 40 nm±10, an average aspect ratio of around 3±1 for the protuberances or spikes (i.e., branches), and an average of 7±2 branches per object/particle without accounting for hyperbranching. The gold nanostars 10 exhibit a broad localized surface plasmon resonance (LSPR) peak at around 975 nm.

While the systems and methods described herein have largely been described in the context of the nanostructures 10 as gold-based nanostars it should be appreciated that other useful nanostructures 10 with different material compositions, shapes, and morphologies can be used and are contemplated to fall within the scope of the invention. The microfluidic technologies that may be used include fluid-contacting surfaces 22 (e.g., microfluidic channels or capillaries 24) that are formed from glass, silica, silicon, indium tin oxide (ITO), quartz, silicone or any oxide substrate. Flow is controlled through the microfluidic device 10 by connecting one or more pumps 34 as noted herein. For example, computer-controlled syringe pumps 34 such as those illustrated in FIGS. 2A and 2B.

FIG. 2A depicts two such syringe pumps 34 that are used to flow different solutions (e.g., solutions #1 and #2) through one or more microfluidic channels or capillaries 24. This configuration may be used, for example, to grow the nanostructures 10 within the one or more microfluidic channels or capillaries 24 according to one embodiment. FIG. 2B depicts a single syringe pump 34 that is used to flow a sample through the one or more microfluidic channels or capillaries 24. The embodiment of FIG. 2B may also be used to grow the nanostructures 10 for example by mixing the growth solution and reducing agent just prior to flowing through the one or more microfluidic channels or capillaries 24. The sample may include, as one example, a biological fluid such as blood, blood plasma, blood serum, pleural fluid, peritoneal fluid, semen, saliva, sweat, tears, and the like. The biological fluid may, in some instances, be processed (e.g., filtered or subject to chromatographic separation) prior to being run through the device. Alternatively, the biological fluid may be unprocessed in other embodiments.

Nanostructures 10 with the selected materials and morphology, such as gold nanostars are synthetized in situ, i.e., directly along the fluid-contacting surfaces 22 (e.g., internal wall(s) of the capillary or microfluidic channels 24) via scalable, reproducible, and rapid fabrication processes. For gold nanostars, seed-mediated growth of gold branched nanoparticles can be used. In this process, gold seeds 23 (small gold spherical particles having a diameter of less than 3 nm (e.g., around 1-2 nm) are first grafted directly to the walls of the microfluidic channels or capillaries 24 using a chemical coupling agent 25 (in one embodiment a silane coupling agent) such as (3-aminopropyl)triethoxysilane (APTES) followed by carefully controlling the flow rate of a secondary growth solution within the microfluidic device 20. An alternative silane coupling agent 25 to APTES may include mercaptopropyltrimethoxysilane. Polymer-based coupling agents such as polyethyleneimine may also be used. Prior to addition of the coupling agent 25, the one or more microfluidic channels and capillaries 24 are cleaned with piranha solution (3:1 98% sulfuric acid and 30% hydrogen peroxide, Fisher Scientific) sonicated multiple times (e.g., four times) with high performance liquid chromatography (HPLC)-grade water and oven-dried.

To grow the nanostar nanostructures 10 on the seeds 23, a metallic salt precursor is used along with a shape directing agent, a surfactant, and a reducing agent. In one embodiment to grow gold nanostar nanostructures 10, gold salt precursor such as tetrachloroauric acid is used together with shape directing agents such as $AgNO_3$, NaBr, or NaI. A surfactant such as laurylsulfobetaine (LSB), triton-X, cetyltimethylammonium chloride, or cetrimonium bromide may be used. The reducing agent may include, for example, ascorbic acid, sodium citrate, or sodium borohydride. As explained herein, the growth solution may also contain hydrochloric acid which is used to prevent deposition of byproducts due to secondary nucleation. In one preferred embodiment, the growth solution includes a surfactant (N-dodecyl-N,N-dimethyl-3-ammonio-1-propanesulfonate, or lauryl sulfobetaine, LSB), used to stabilize the particles during growth, L-ascorbic acid (AA) as a reducing agent, and silver ions to direct the anisotropic growth. In addition, hydrochloric acid present in the growth solution is used to control the reducing power of AA and therefore the growth kinetics of the gold crystals.

Figure 3:
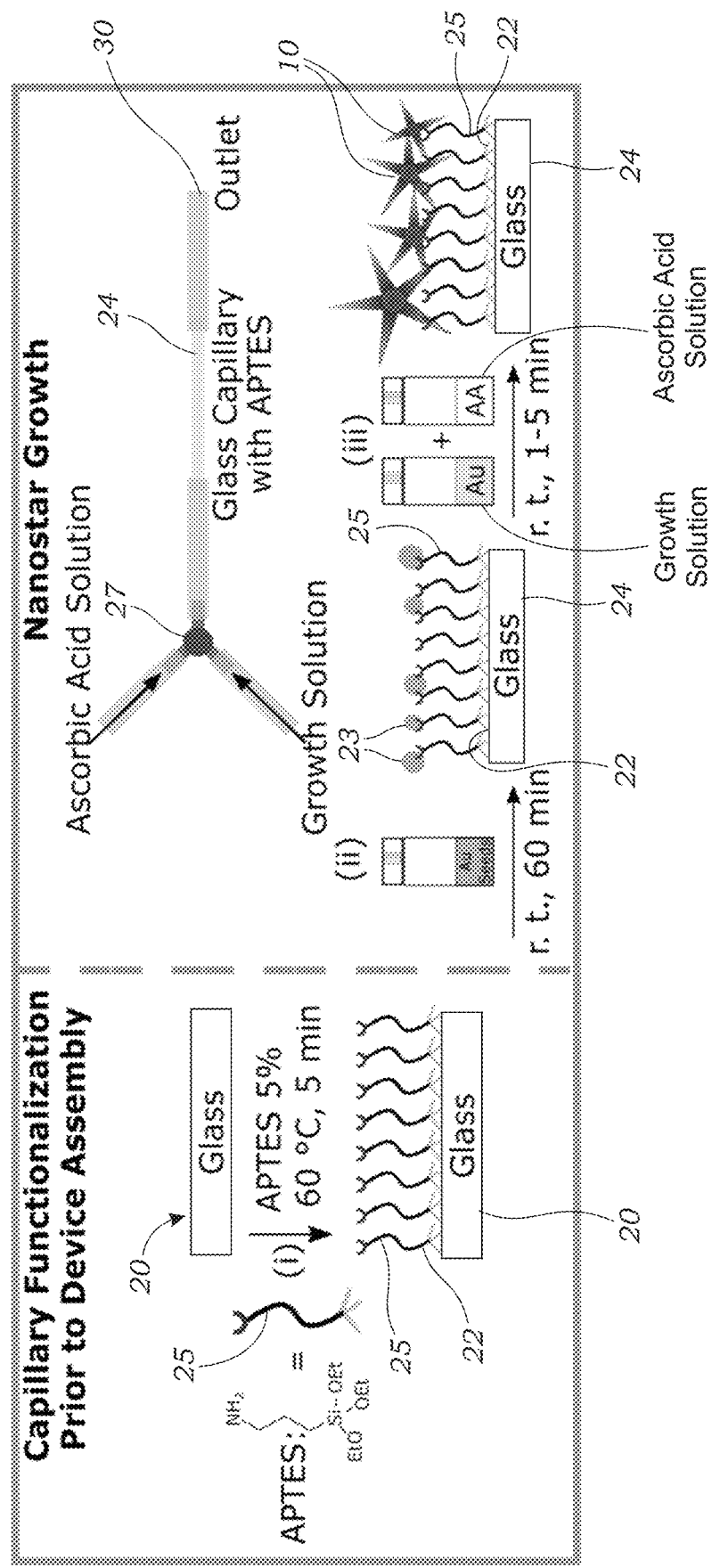
FIG. 3 schematically illustrates the two-step process to prepare a microfluidic channel or capillary that is populated with nanostructures. The first process (left) involves depositing a chemical coupling agent on a substrate. The second process (right) involves seeding the inner surface(s) of the microfluidic channel or capillary with seeds followed by exposure to a flowing growth solution to grow the nanostructures on the deposited seeds.

With reference to FIG. 3, one embodiment of how the gold nanostar nanostructures 10 are formed in situ on the internal surface(s) 22 of the one or more microfluidic channels or capillaries 24 includes the following operations. First, the one or more glass microfluidic channels or capillaries 24 are functionalized with a coupling agent 25 that in one preferred embodiment is a silane coupling agent. An example of the use of such a silane coupling agent includes APTES (5% v/v in ethanol, 60° C.) which is exposed to the glass microfluidic channels or capillaries 24 for about 5 min. The APTES-coated microfluidic channels or capillaries 24 may also be sonicated in ethanol three times for 5 min, and stored in ethanol.

The microfluidic channels or capillaries 24 may have any number of sizes and shapes. In the experiments described herein, rectangular capillary channels 24 were employed that were 1-2 mm wide, a height of 100 μm, and a length of several centimeters. Of course, it should be appreciated that any number of cross-sectional shapes (and sizes) can be used for the microfluidic channels or capillaries 24. These include rectangular, square, semi-circular, and circular cross-sections. The length of the microfluidic channels or capillaries 24 may also vary. For example, for cell-based uses, the cross-sectional area may be square with cross-sectional dimensions between about 80 μm and about 100 μm although other dimensions may also work. In addition, in some embodiments, all internal surfaces 22 of the microfluidic channel or capillary 24 is populated with gold nanostar nanostructures 10. In other embodiments, fewer than all internal surfaces 22 of the microfluidic channel or capillary 24 is populated with gold nanostars 10 (e.g., four-sided capillary or channel has only one side or part of one side populated with gold nanostars 10).

After depositing the silane coupling agent 25 onto the internal surfaces 22 (left side of FIG. 3), the one or more glass microfluidic channels or capillaries 24 are rinsed by passing 5 mL of water therethrough with a syringe. In one embodiment, a solution of cetyltrimethylammonium chloride (CTAC)-coated gold seeds 23 is incubated in the one or more microfluidic channels or capillaries 24 for 1 hr at room temperature. CTAC-capped seeds 23 may be prepared by adding 4.7 mL of 0.1 M CTAC with 25 μL $HAuCl_4$, followed by addition of 300 μL of 10 mM $NaBH_4$ under vigorous magnetic stirring. The one or more microfluidic channels and capillaries 24 may be dried with nitrogen before use. A solution of CTAC-coated seeds is flowed into the one or more microfluidic channels and capillaries 24 at 0.100 mL/min/microfluidic channel or capillary using a syringe pump and was incubated in the capillary for 1 hr. The microfluidic channels and capillaries 24 may be hand-rinsed with water using a syringe.

Of course, other coating materials besides CTAC may also be used such as LSB although LSB-capped seeds 23 generally produced a higher variation in the position and extinction of the LSPR peaks. To grow the gold on the seeds 23, water was again flowed through the capillary 24 with a syringe before flowing the two separate ascorbic acid and gold precursor solutions (AA Solution and Growth Solution) through the Y-split 27 to the capillary 24 at a total flow rate of 500 μL/min for 2 minutes (flow rate split into 250 μL/min for each separate line, for 1 mm wide channels). As shown in FIGS. 2A and 3, two separate solutions (solution #1 and solution #2) are flowed through the one or more microfluidic channels or capillaries 24 at room temperature (r.t.) for 1-5 minutes with the solutions being mixed or combined just prior to entry into the one or more microfluidic channels or capillaries 24. The first syringe (containing solution #1 in FIG. 2A) contains 4 mL 0.1 M LSB, 120 μL of 50 mM $HAuCl_4·3H_2O$, and 120 μL of 10 mM $AgNO_3$. The second syringe (containing solution #2 in FIG. 2A) contains 4 mL 0.1 M LSB, 80 μL 1 M HCl, 400 μL of 100 mM AA. The one or more microfluidic channels or capillaries appear dark blue to the naked eye due to the growth of the gold nanostars 10.

In the embodiment illustrated in FIGS. 2A and 3, two separate solutions (solutions #1 and #2) are input by separate syringes and the fluid is combined in the Y-split 27 just prior to entering the one or more microfluidic channels or capillaries 24 to grow the nanostructure 10. In an alternative embodiment, the Y-split 27 is omitted and the growth solution and the ascorbic acid solution are mixed just prior to being flowed through the one or more microfluidic channels or capillaries 24 (the one or more microfluidic channels or capillaries 24 are already seeded with seeds 23 as described herein). Thus, a single syringe or pump 34 can be used to push this mixed fluid through the one or more microfluidic channels or capillaries 24 (like illustrated in FIG. 2B).

In this embodiment, a growth solution is prepared containing 4 mL 0.1 M LSB, 60 μL of 50 mM $HAuCl_4·3H_2O$, and 60 μL of 10 mM $AgNO_3$ and 40 μL 1 M HCl. Just prior to forming the mixture of the growth solution and ascorbic acid solution (less than a few minutes), an aliquot of 200 μL of 100 mM AA was added to the growth solution and stirred and loaded into the syringe pump 34 which then pumped the combined or mixed solution through the one or more microfluidic channels or capillaries 24. The flow rate of the mixed growth solution within the one or more microfluidic channels or capillaries 24 may vary depending on the size of the one or more microfluidic channels or capillaries 24. Generally, the flow rate of the mixed growth solution may be between about 0.125 4/min-about 500 μL/min for 1-5 minutes. For example, using a single capillary 24 of dimensions 1 mm×100 μL (internal diameter) a flow rate of 250 μL/min was used and produced good results.

The amount of time and the flow rate that the mixed growth solution (containing the reducing agent) is flowed through the device 20 may vary. Typically, the mixed growth solution is flowed through the one or more microfluidic channels or capillaries 24 is several minutes long (e.g., 3 minutes). Likewise, the flow rate may vary as noted above about 0.125 µL/min-about 500 µL/min. It was experimentally found, for example, that using a 100 µm capillary 24, gold nanostars 10 grown for short time periods (FIG. 4A) produced nanostructures with no branching (see FIGS. 4A-4J), likely due to insufficient amounts of growth solution flowed through the capillary 24. Those grown for greater than 6 minutes (FIGS. 4D and 4E) at the same rate produced overgrown nanoparticle films, consistent with the introduction of excess gold. The lowest and highest flow rate both yielded products with similar morphologies (FIGS. 4F and 4J). The optimum or standard growth time and flow rate used for the 100 µm capillary 24 was a growth time of 3 minutes and a flow rate of 250 µL/min.

After formation of the one or more capillaries or microfluidic channels 24 populated with the gold nanostructures 10, the nanostructures 10 may be functionalized with one or more binding molecules or ligands that are used to bind a cell 110 or other molecule 100. Binding molecules and ligands of various types are well known to those skilled in the art and may include antibodies, proteins, aptamers, or other capture ligands or probes. The molecule that is to be captured 100 may include, way of illustration and not limitation, a biomolecule, small molecules, drug, metabolite, analyte, or the like. For example, thiol linkages with the gold nanostructures 10 may be used to tether capture ligands to the gold nanostructures (which are also flowed through the device), exploiting the utility and strength of the thiol-gold bond. In one preferred embodiment, an antibody may be tethered to the gold nanostructures 10 to capture cells 110, e.g., cancer cells 110 like CTCs. It should be appreciated that this strategy can be adapted easily for antibodies, aptamers, other relevant biomolecules, and/or other chemical functionality that can be used for selective recognition of different cancer cells 110 (or other types of cells 110) or specificity. For example, the capture ligand or binding molecule may be specific to circulating fetal cells obtained from maternal circulation.

In one preferred embodiment, the plasmon resonance associated with the nanostructures 10 obtained via this process is tuned to the near-infrared (NIR) biological window, varying the concentration of silver, and the concentration and reducing power of AA (FIGS. 5A-5E). The NIR window generally spans from about 750 nm to about 2,500 nm and the biological NIR window, which may be a smaller range of overlapping wavelengths, e.g., about 650 nm to about 1350 nm. Moreover, these nanostructures 10 are particularly efficient in generating localized heat through phonon coupling with absorbed infrared (IR) photons, which is used as described herein for the selective capture and release of cells 110.

The aforementioned seed-mediated nanoparticle synthesis protocol has been tailored in order to generate branched gold nanoparticles 10 and to optimize the shape-yield and the plasmon band position of the final product. The method also minimizes secondary nucleation to enable controlled growth of the nanostructures 10 in situ. The gold nanostar particles 10 were characterized by ultraviolet-visible (UV-vis) spectroscopy and transmission electron microscopy (TEM) as seen in FIGS. 5B-5E, 6A and 6B. For characterization, a CARY 50 UV-visible spectrophotometer was used for spectroscopic characterization of colloidal solutions and capillaries. The aspect ratio and distribution of products for the nanoparticles synthesized in solution was probed with TEM. Samples were prepared by centrifuging 10 mL of the final solution at 15,000 rpm for 20 min, followed by removal of the supernatant. The sample was redispersed in 10 mL of water, and 1.0-1.1 mg of PEG-SH was added. The solution was left to stir on an orbital shaker for 2 hr. Afterwards, the solution was washed by centrifuging 4 mL at 15,000 rpm for 20 min, removing the supernatant, and redispersing in 4 mL in milliQ water. The rinsing step was carried out 4 times for gold nanostars 10 synthesized with CTAC-coated seeds, and 2 times for gold nanostars 10 with LSB-coated seeds. After the final rinsing step, the particles 10 were redispersed in 5 µL of milliQ water. A 400-mesh Cu grid with carbon support (Ted Pella, Inc.) was placed in a petri dish lined with parafilm, and a 5 µL drop of the washed gold nanostars 10 was placed on the grid. The petri dish was closed and covered with parafilm to allow for slow evaporation of the drop over 4 hr. If the drop was not visibly dry 2 hr prior to taking TEM measurements, the parafilm was removed. TEM was carried out at 120 kV with the FEI Technai 12 (T12). The morphology and uniformity for the gold nanostars 10 grown in the capillaries 24 were probed with scanning electron microscopy (SEM), obtained with a ZEISS Supra 40VP SEM.

Figure 6A:
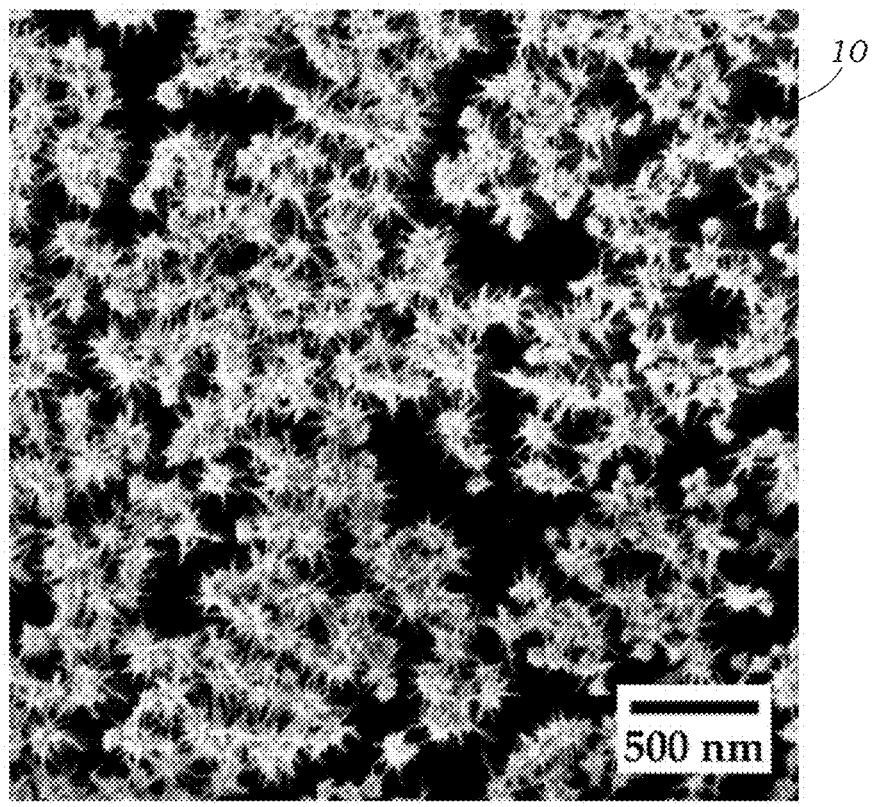
FIGS. 6A and 6B illustrate transmission electron micrographs demonstrating the morphology of the gold nanostars (FIG. 6A) grown with microfluidics and the uniformity in density of the synthesized gold nanostars (FIG. 6B) within the capillary.
Figure 6B:
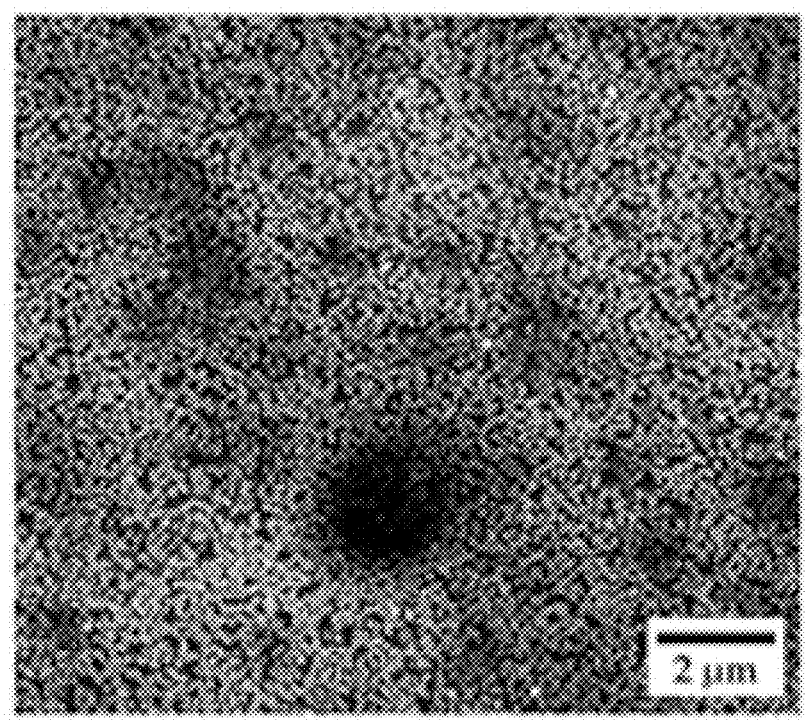
Figures 7A, 7B:
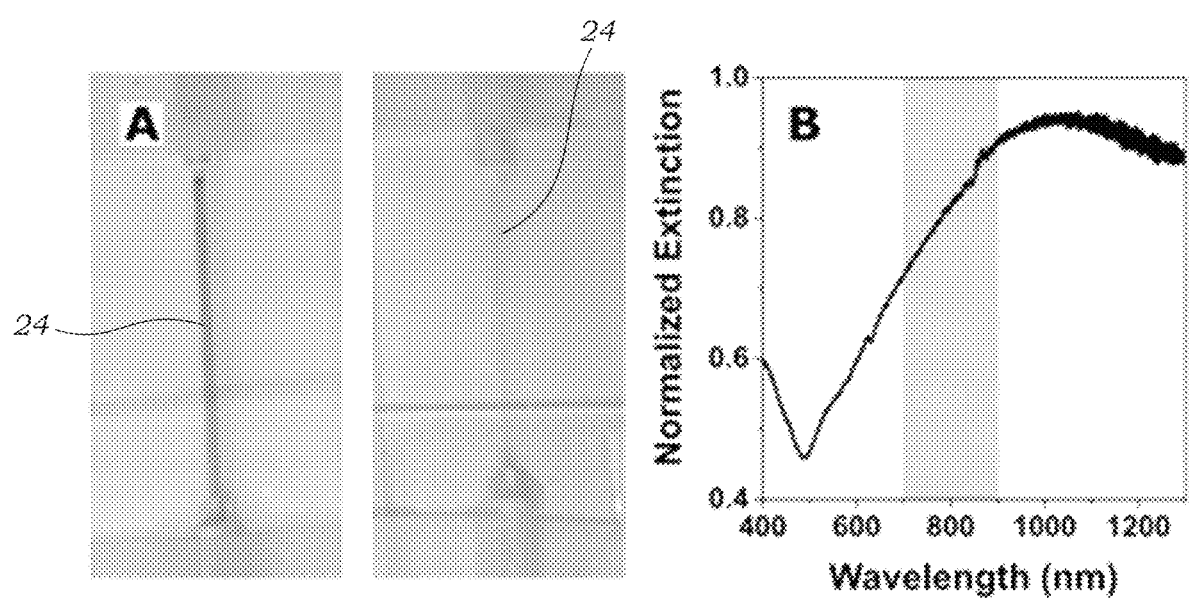
FIG. 7A illustrates photographs of 1 mm capillaries (left) with and (right) without adding cetyltrimethylammonium chloride-coated seeds after flowing the reducing agent solution and the growth solution through the capillary.
FIG. 7B illustrates ultraviolet-visible spectra of capillaries functionalized with cetyltrimethylammonium chloride-coated seeds after growth. The shaded area represents the biological NIR window.

FIG. 7A illustrates how growth of the gold nanostructures needs initial seeding of the glass capillaries with CTAC-coated seeds. The left image has been seeded while the right image of FIG. 7A was not seeded (only the left image shows the intense blue color showing the plasmonic response). FIG. 7B illustrates the UV-visible absorption profile of gold nanostars 10 grown in situ on the internal walls 22 of glass capillaries 24, together with the biological NIR window (darkened region) that for CTAC-coated seeds 23. Nanoparticle 10 growth was verified taking place at the gold seeds 23 anchored to the APTES monolayer 25 rather than due to deposition of particles resulting from secondary nucleation. After in situ growth, glass surfaces have an intense blue color and with UV-vis spectra demonstrating a broad plasmonic band spanning the entire NIR biological window (FIGS. 7A and 7B), in which damage to biomolecules, biomolecular assemblies, and cells is minimized. Scanning electron microscopy (SEM) analysis confirms the presence of anisotropic gold nanoparticles 10 on the seed-APTES-functionalized surface (FIGS. 6A, 6B). This branched nanostructure interface offers unique capabilities that enable highly scalable diagnostic technologies for capturing and analyzing cells 110 such as circulating tumor cells (CTCs) and other targets of interest.

The surface chemistry of the branched gold nanostructures 10 can be tailored to enable the selective capture a wide range of biomolecular and cellular targets. For example, there is emerging interest in utilizing CTCs, which detach from primary or metastatic lesions and circulate throughout the body as "liquid biopsies" to provide early diagnosis and real-time information regarding patients' disease status. However, CTCs are difficult to detect due to their relative low abundance in peripheral blood. The efficient isolation of CTCs via this approach will drive innovation in many clinically relevant applications relating to disease monitoring and development of new treatments.

Figure 8A:
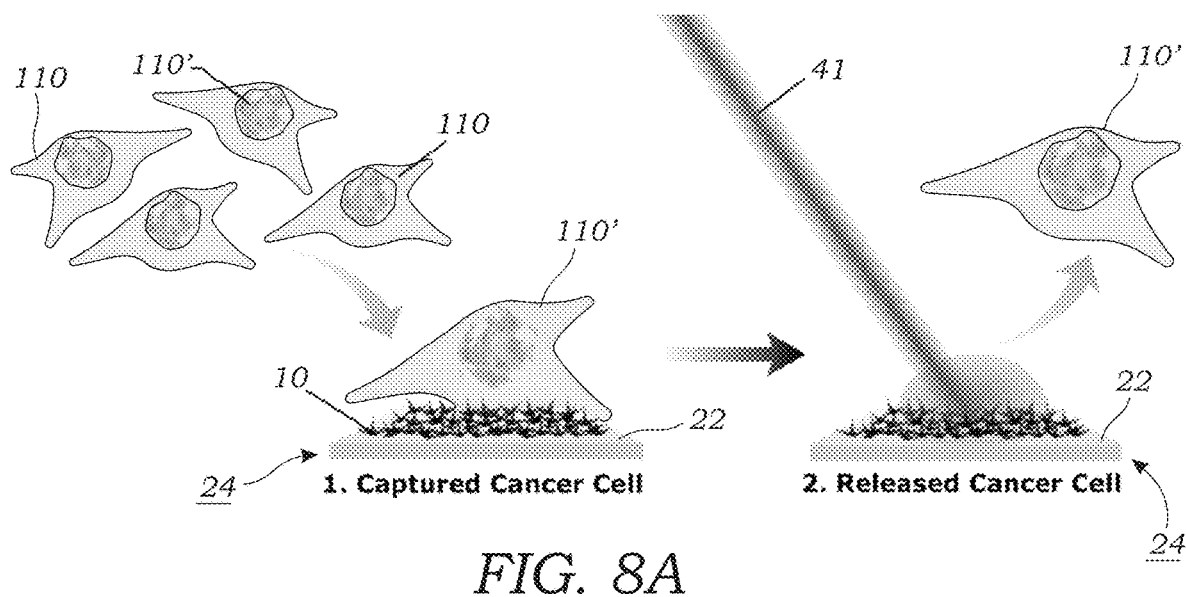
FIG. 8A schematically illustrates how a cancer cell (e.g., CTC) among healthy cells is captured on the gold nanostars that are functionalized with a binding molecule such antibody specific to the cancer cell. The right side of FIG. 8 also illustrates how a laser beam is used to create localized heating to release the cancer cell from the surface. The cancer cell can then flow downstream for capture, analysis, and/or disposal.
Figure 8B:
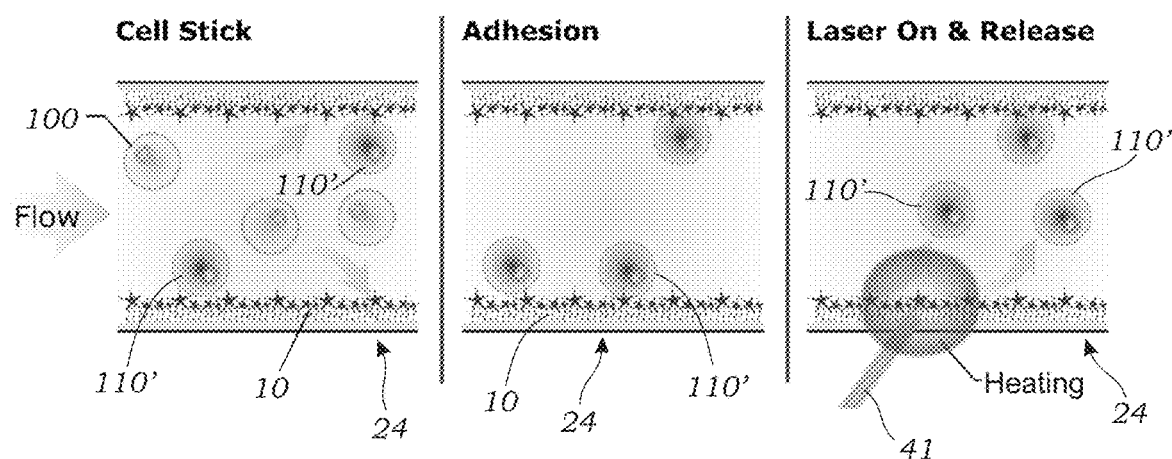
FIG. 8B schematically illustrates a sequence of flowing a solution containing healthy cells and cancer cells through a microfluidic channel or capillary that contains gold nanostars populated along the surfaces thereof that are functionalized to capture cancer cells. The cancer cells adhere to the inner surface of the microfluidic channel or capillary and are released after the surface is irradiated with a laser.

FIG. 8A illustrates schematically, how the one or more microfluidic channels or capillaries 24 having the gold nanostars 10 on the inner surface(s) 22 are used to capture cancer cells 110' (or other specific cells 110). The gold nanostars 10 include a capture ligand that is selective to a particular cell type such as a cancer cell 110' (e.g., CTC). The cancer cell 110' is first captured on the gold nanostars 10 followed by irradiation with a beam of light 41 (e.g., from a light source 40 such as a laser 40) to cause localized heating which effectuates release of the cancer cell 110'. FIG. 8B illustrates a sequence of flowing a solution containing healthy cells 110 and cancer cells 110' through a capillary or microfluidic channel 24 that contains gold nanostars 10 populated along the surfaces thereof (in this embodiment with thiol-terminated poly(ethylene glycol) (PEG-SH, which substitutes for LSB and prevents non-specific adsorption of healthy cells 110)). The gold nanostars 10 are functionalized with a capture ligand specific to the cancer cells (e.g., an antibody, aptamer, or the like), which thereby adhere to the nanostructures 10 in the device. In one particular embodiment, the light source 40 is a laser such as that illustrated in FIG. 8B is used to generate a beam of light 41 that is used to create localized heating at the surface where the nanostructures 10 are located to release the adherent cells 110 where the cells 110 can flow downstream for capture, analysis, and/or disposal. An exemplary laser 40 includes a pulsed Ti:sapphire laser with 200 fs pulse and 76 MHz repetition rate at 700 nm to 1000 nm wavelengths. The wavelength of the laser 40 used in the data disclosed herein was 785 nm. While a pulsed laser was used for the data herein, it should be appreciated that a continuous or non-pulsed laser may also be used.

While the beam of light 41 has largely been described as being formed by a light source 40 in the form of a laser it should be appreciated that other light sources 40 may be used to create the beam of light 41 that is capable of creating localized heating conditions on the inner surface(s) 22 populated with the nanofeatures 10. For example, other light sources 40 such as light emitting diodes (LEDs) or laser diodes may be used to generate the beam of light 41 in alternative embodiments.

As one example, the Ewing sarcoma (EWS) family of tumors, the second most common bone cancer in children, manifests as aggressive bone and soft tissue lesions with high propensity for metastasis and particularly poor prognosis. Difficulties arise from limitations in the current surveillance imaging strategies used to monitor progression of these cancers, which often detect the spread of the disease too late for effective treatment. The surfaces of the nanostars 10 can be modified using antibody anti-LINGO-1 specific to bind surface protein LINGO1, a protein that has been recently identified as a specific EWS biomarker. For example, LINGO-1 antibody may be obtained from Novus Biologicals (catalog number NBP2-19359). Other LINGO-1 antibodies are known such as those in U.S. Pat. No. 8,058,406, which is incorporated by reference herein.

Once captured, the cells 110' that adhere to the gold nanostars 10 can be recovered and released for further characterization via hyperthermia-mediated-cell-detachment illustrated in FIGS. 8A and 8B. Localized heating by a beam of light 41 releases the cells 110 back into the bulk fluid where they can flow downstream. In one embodiment, the beam of light 41 may scan (e.g., in a raster manner) across the one or more microfluidic channels or capillaries 24 to release the cells 110. Optical rastering by the light source 40 (e.g., laser) using moving mirrors and lens can be used to scan across the microfluidic device 20 in the x, y, and z (depth) directions. Alternatively, the microfluidic device 20 itself may be moved relative to a stationary beam of light 41 to achieve similar scanning results. For example, the microfluidic device 20 may be mounted on a moveable stage or the like. This capability further provides a general solution for the prevention of clogging and fouling of the microfluidic flow network (e.g., microfluidic channels and capillaries 24), which commonly leads to device failure during long-term operation. One of the most powerful aspects of the platform is its potential to capture and then to release CTCs 110 from a variety of malignancies that rely on serial radiographic imaging protocols to monitor for disease progression and/or metastasis (e.g., neuroblastoma, Wilms tumor, etc.).

Figure 9:
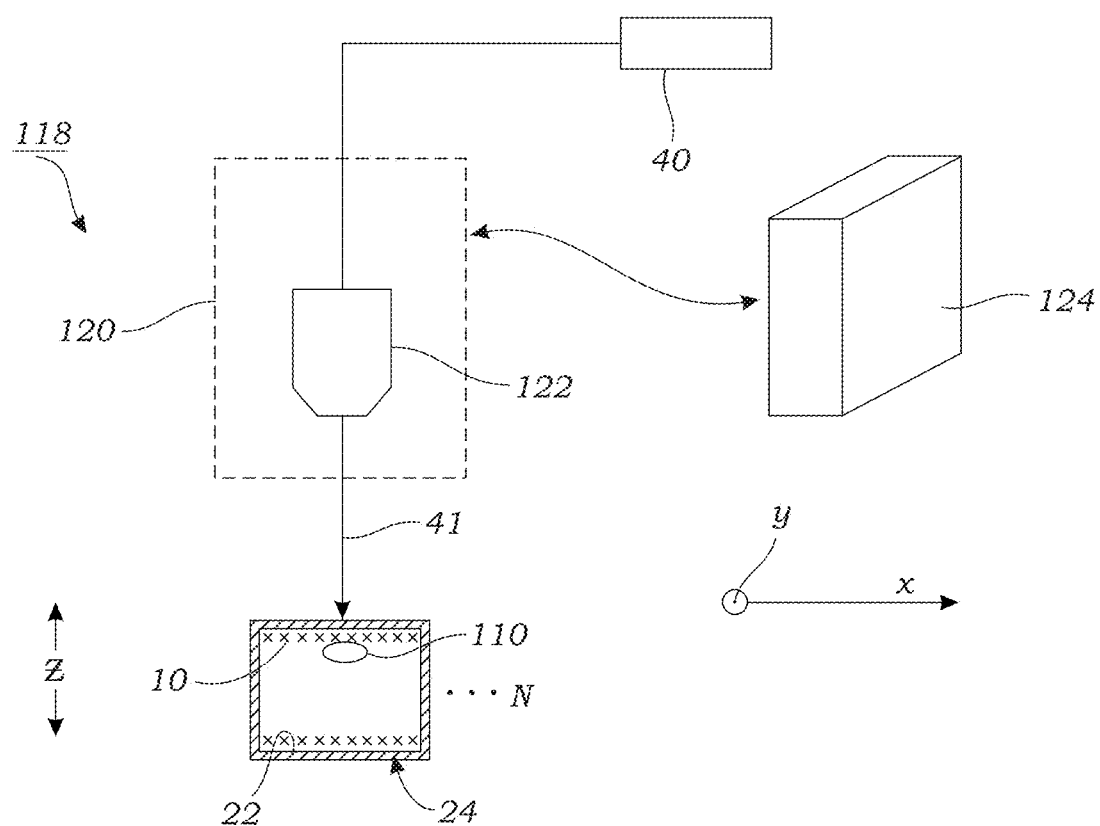
FIG. 9 schematically illustrates one embodiment of a system that is used to capture and release specific cells of interest. The system uses an optical microscope to visually identify adhered cells. A laser is provided to irradiate the microfluidic device to selectively release the cells back into the microfluidic channel or capillary.

FIG. 9 illustrates one embodiment of a system 118 that is used to capture and release specific cells 110 of interest. In this embodiment, one or more microfluidic channels or capillaries 24 (FIG. 9 illustrates N such microfluidic channels or capillaries) are populated with the nanostructures 10 (e.g., gold nanostars 10) functionalized with a capture ligand specific to a specific cell type (e.g., CTCs). For example, the microfluidic channel or capillary 24 may include a rectangular-shaped cross-section in which two of the inner surfaces 22 (e.g., top and bottom) contain gold nanostars 10 that are functionalized with capture ligands specific to CTCs. An optical microscope 120 is provided which may optionally obtain fluorescent images in additional to standard non-fluorescent images of small objects such as cells 110. The optical microscope includes focusing optics 122, which is used to focus on different optical planes (e.g., the top or bottom surfaces 22 in the z direction). In one embodiment, the microfluidic device 20 that contains the one or more microfluidic channels or capillaries 24 is disposed on a moveable stage so that the different areas of the microfluidic channels or capillaries 24 may be observed (e.g., x and y scanning) with the optical microscope 120. Alternatively, the microfluidic device 20 may remain stationary while the optics of the optical microscope 120 scan the sample in the x and y directions. The optical microscope 120 is used to locate individual cells 110 that are adhered to the inner surfaces 22 of the one or more microfluidic channels or capillaries 24. In some embodiments, the adhered cells 110 are also labelled with a fluorescent probe, label, or dye to further aid in locating the cells 110. However, in other embodiments, the individual cells 110 are unlabeled.

Once the location of the cells 110 have been identified, the system 118 triggers a light source 40 that delivers a beam of light 41 through the same optics (e.g., focusing optics 122) to deliver a focused beam of light on surface 22 containing the adherent cells 110. The light source 40 (e.g., laser) delivers a continuous or a pulsed beam of light 41 for a period of time (e.g., seconds to minutes), which produces localized heating at the surface 22 caused by the plasmonic nanostructures 10. The localized heat then causes conformational changes in the nanostructures 10 which liberates the adherent cell 110. Reshaping of the cells 110 and the formation of microbubbles may also affect the release of cells 110. It should be noted that while the light source 40 is activated, fluid is flowing through the one or more microfluidic channels or capillaries 24. As explained herein, the flow of fluid within the one or more microfluidic channels or capillaries 24 reduces the buildup of excess heat and allows the removal of the liberated cells 110 as the cells exit with the flowing fluid. A computing device 124 may be used to control various aspects of the device including but not limited to: scanning of the one or more microfluidic channels or capillaries 24, actuation and power levels of the light source 40, flow rates of pump(s) 34, focusing optics 122, and the like. The system 118 may operate by locating all of the cells 110 first within the one or more microfluidic channels or capillaries 24 followed by a separate operation where each location is then subject to laser illumination. The location(s) of the cells 110 may be stored and then the microfluidic device 20 or optics are moved to irradiate the surface(s) 22 each stored location(s). Alternatively, as each cell 110 is located using the optical microscope 120, the light source 40 may be activated immediately after location of the cell 110.

Figure 10A:
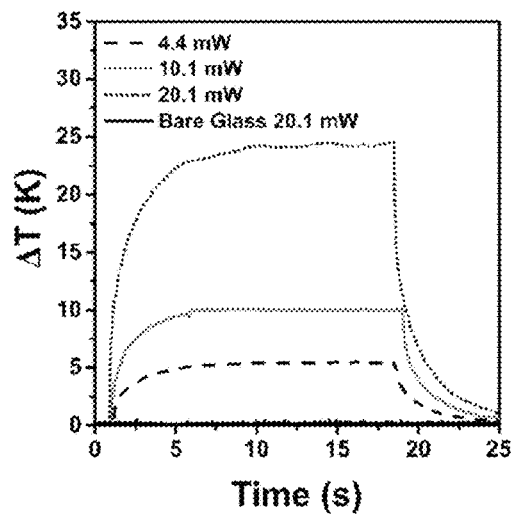
FIGS. 10A and 10B illustrate graphs showing changes in temperature with irradiation time at different laser irradiation power densities in no flow (FIG. 10A) and flow conditions (FIG. 10B).
Figure 10C:
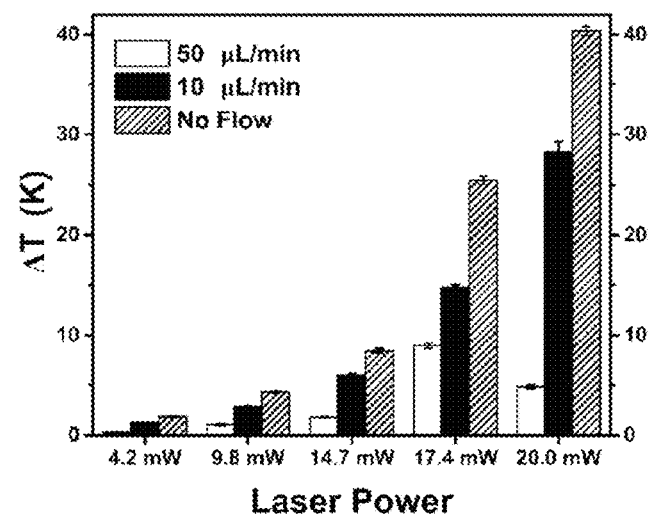
FIG. 10C illustrates a histogram showing average change in temperature as a function of laser power for different flow rates.
Figure 10B:
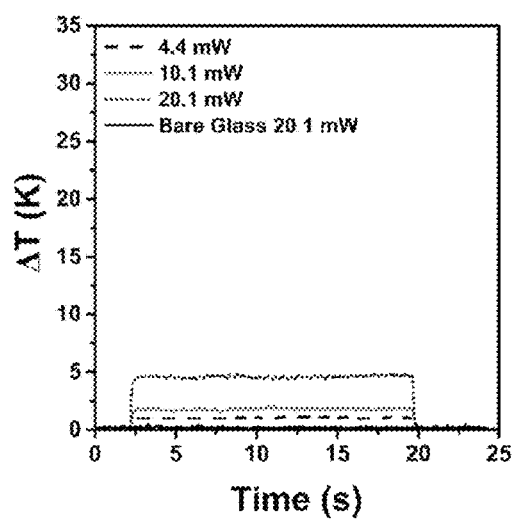
Figure 10D:
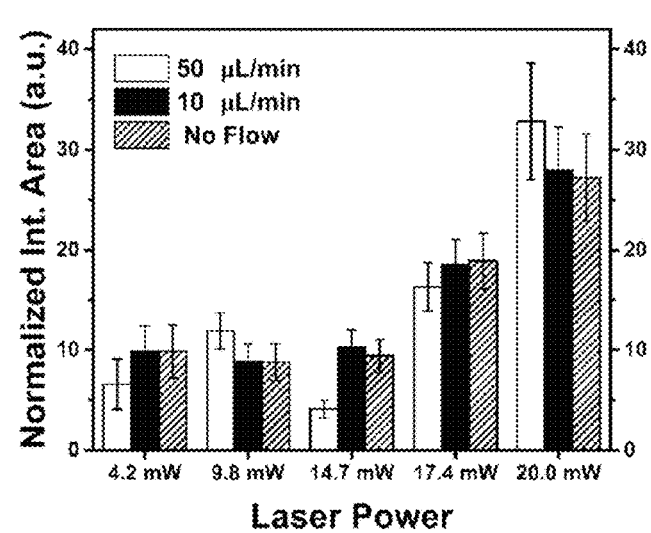
FIG. 10D illustrates a histogram of normalized integrated peak area for the 1575 cm$^{-1}$ thiophenol surface-enhanced Raman scattering peak.

The heating imparted by the beam of light 41 from the light source 40 can be tuned by changing power and flow conditions as a function of power and flow rate. Macroscale temperature changes of around 40° C. were observed in "no flow" conditions within a 100 μm capillary 24 illuminated with a laser light source 40, compared to temperature increases under 10° C. in flow, which is approximately 30° C. lower at the highest laser power tested compared to no flow conditions (FIGS. 10A-10B). This is due to the cooling effect in flow conditions, where the flowing water serves as a heat sink as the generated heat is carried away from the area under laser irradiation. (compare FIGS. 10A and 10B). Furthermore, equilibrium temperature was reached after ~10 s of irradiation in no flow conditions, where no flow conditions reached equilibrium temperature in less than 1 s (FIGS. 10E and 10F). FIG. 10C illustrates how higher power laser irradiation results in increased temperature changes with the highest change occurring in the no flow condition. Macroscale temperature change is decreased significantly in flow vs. no flow conditions. Surface-enhanced Raman spectroscopy (SERS) was utilized to probe the nanoscale environment in complement to the macroscale information obtained with the thermal measurements. Although the temperature is significantly decreased in flow conditions, the overall SERS intensity is comparable in flow and no flow at variable power densities. For example, FIG. 10D illustrates SERS intensity of thiophenol bound to gold nanostars 10. The SERS intensity was largely comparable regardless of flow rate. This indicates that even in flow, the gold nanostars 10 are able to generate the same amount of heat as in the no flow case.

Figures 11A, 11B, 11C:
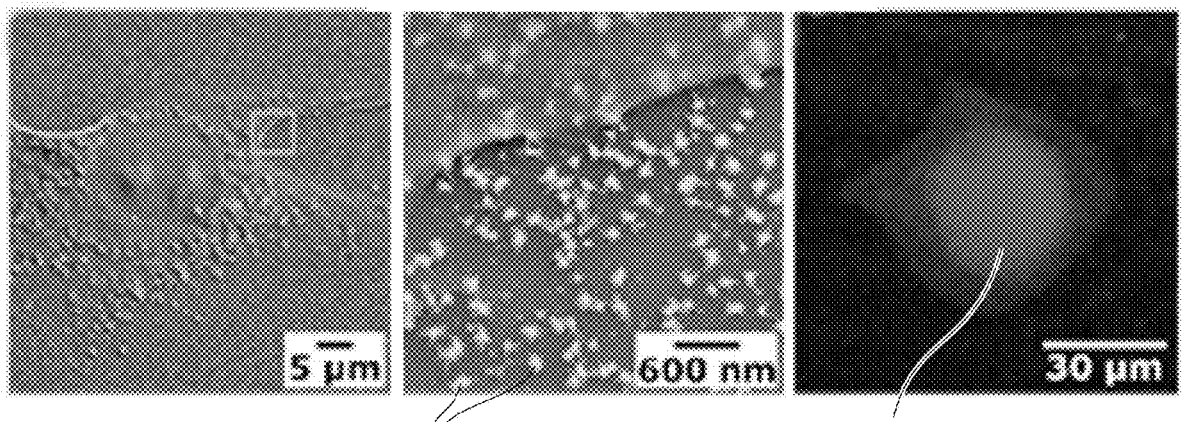
FIGS. 11A and 11B illustrates scanning electron micrographs of fixed U87-GFP glioblastoma cell on gold nanostar-coated capillaries.
FIG. 11C illustrates a laser-scanning confocal fluorescence microscopic image showing cell spreading after 1 hour of incubation in the gold nanostar-coated capillary.
Figure 11D:
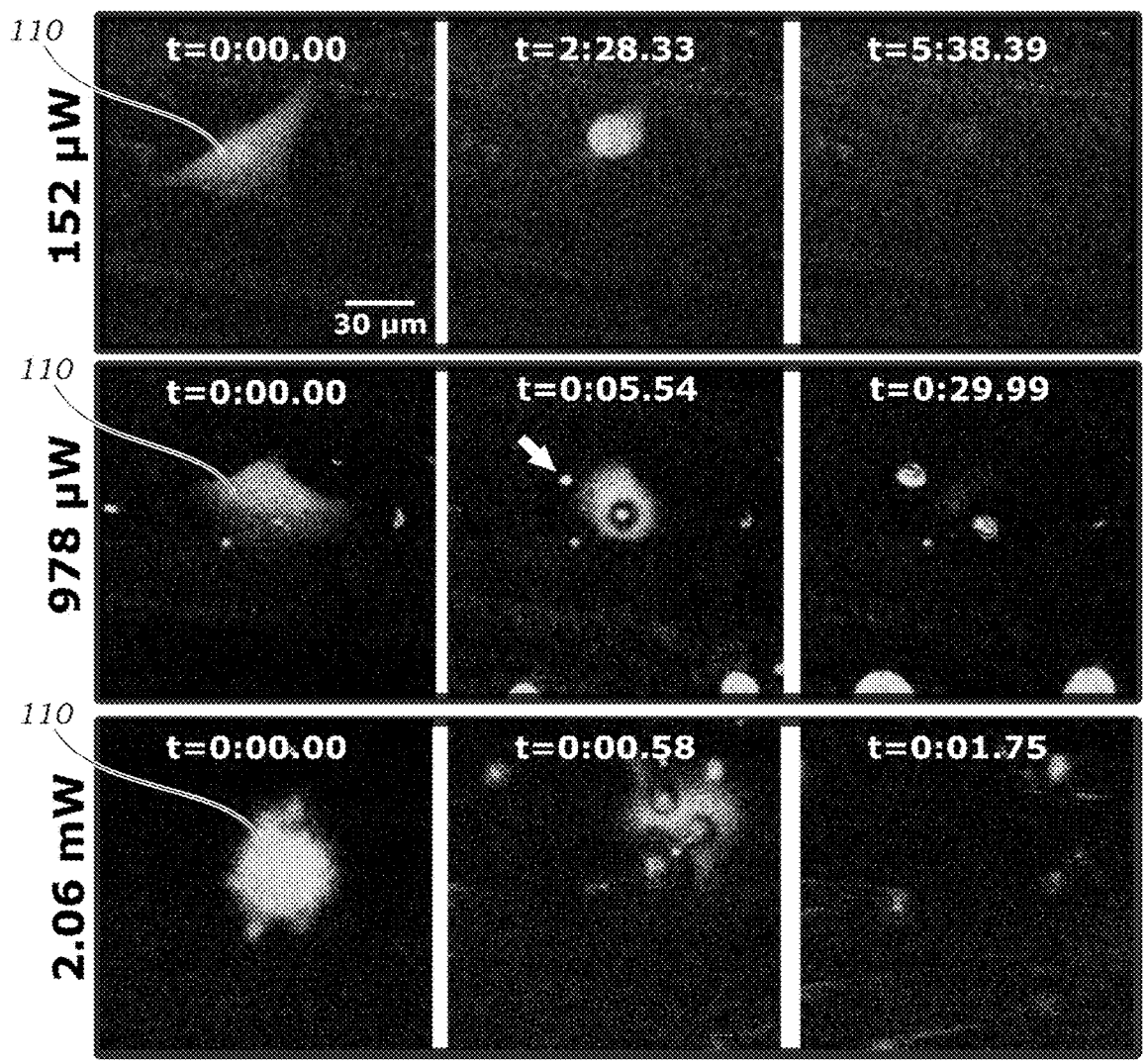
FIG. 11D illustrates time lapse of confocal fluorescence microscopic images of cell removal under irradiation at different laser powers.
Figure 11E:
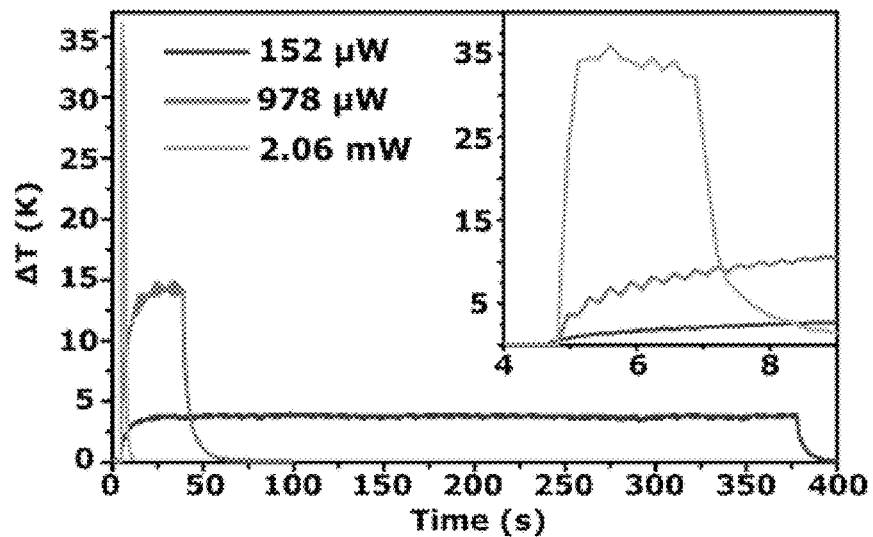
FIG. 11E illustrates a graph of the simultaneously collected thermal measurements (of FIG. 11D) over time in no flow conditions. Inset illustrates larger view of ten second period.

As noted herein, the localized heating imparted by the laser 40 can be used for the hyperthermia-mediated release of grafted adherent cells from the gold nanostar 10 functionalized capillary 24. A 4 cm×100 μm×1 mm glass capillary was formed with gold nanostars 10 formed therein as described herein. The gold nanostars 10 were further functionalized with mercaptoundecanoic acid (in place of LSB) and fibronectin. The presence of fibronectin facilitated cellular adhesion. Glioblastoma cells (U-87 GFP) were then introduced into the functionalized capillary 24 at 10 μL/minute and cell adhesion and spreading were observed in about one hour (FIGS. 11A-11C). Laser irradiation was used to remove cells 110. Different phenomena were observed such as cell morphology changes and microbubble formation depending on the flow rate and laser power. The interaction of adherent glioblastoma cells (U-87 GFP) was monitored using fluorescence confocal microscopy from 0-1.5 hr following introduction of cells 110 into the capillary 24, and the interactions of the cells 110 with the gold nanostars 10 after 24 hr (at 37° C., 95% humidity, 5% $CO_2$) were probed with SEM and fluorescence confocal microscopy. FIG. 11D illustrates time-lapse images of confocal fluorescence microscope images of cell removal under irradiation at different laser powers (152 μW, 978 μW, 2.06 mW) under no flow conditions (i.e., no flow of fluid through the capillary 24 containing the cells 110). FIG. 11E illustrates simultaneous thermal measurements taken with the different laser powers. At low power (152 μW) the laser is powered for almost 6 minutes to liberate cells 110 while at the high power (2.06 mW) the cells 110 are liberated within 2 seconds. The rapid power spike is seen for the highest power.

Figure 12:
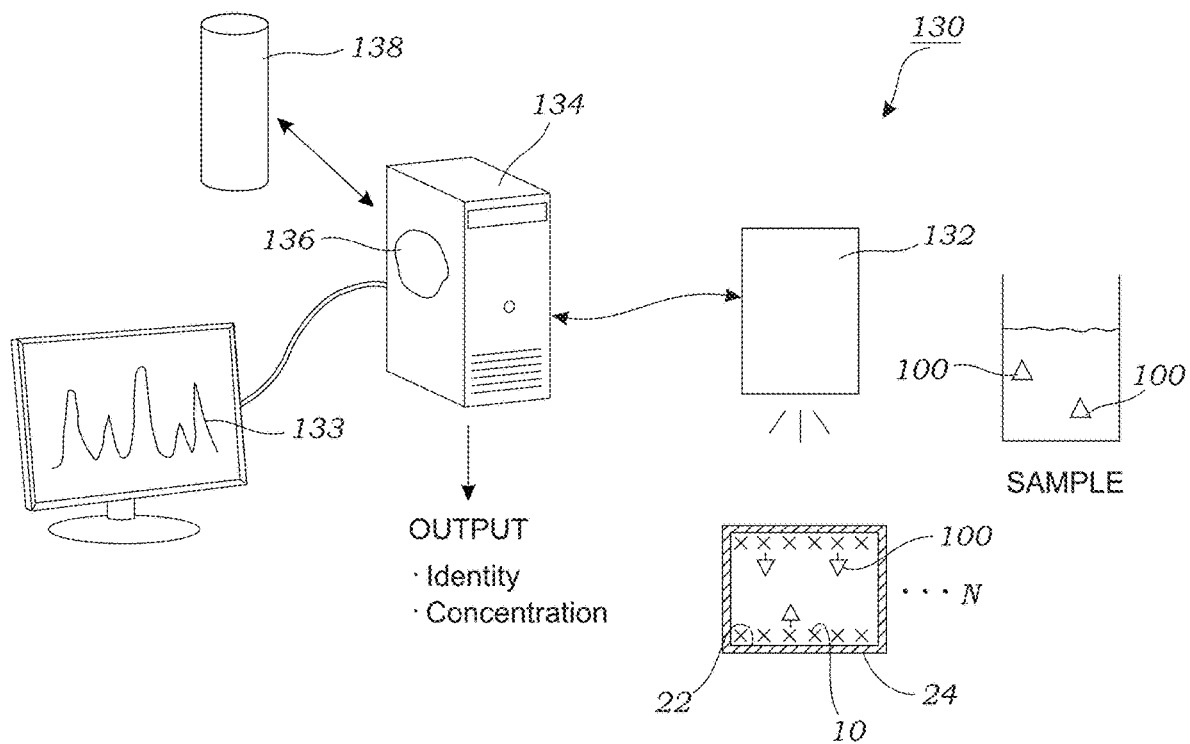
FIG. 12 illustrates one embodiment of a system that is used to enable real-time monitoring and concentration of a target molecule, compound, or other material.

The nanostructures 10 can also be used to enable real-time monitoring and concentration of a target molecule or compound 100 (or other material). The target molecule or compound may include drugs and other biologically relevant compounds of interest in patients' biofluids or other sample (identified as "Sample"). This strategy is illustrated in the system 130 of FIG. 12. In FIG. 12, a SERS spectrometer device 132 obtains SERS spectra 133 (i.e., Raman spectra) from molecules bound or adhered to one or more surfaces 22 of the interrogated capillary or microfluidic channel 24. In this embodiment, one or more microfluidic channels or capillaries 24 are populated with the nanostructures 10 (e.g., gold nanostars 10) functionalized with a capture ligand specific to the target molecule or compound 100 of interest. In some embodiments, only a single surface 22 is interrogated. In other embodiments, for example, where the focal point or region is larger, multiple surfaces 22 (e.g., top and bottom) may be simultaneously or serially interrogated.

A standard curve for calibration of detection performance can be created whereby a series of surface-enhanced Raman spectroscopy (SERS) measurements are acquired of a target molecule/compound 100 in simulated biofluids. The standard curve is based on acquiring reference SERS spectra 133 of the target molecule or compound 100 at various concentrations. The SERS technique is a chemical fingerprint method as the peaks are due to molecular vibrations and are thus characteristic of the functional groups in the molecule(s) and thus its (their) identity. The acquired SERS spectra 133 have peak locations and relative intensities that are compared to corresponding reference SERS spectra 133, which contain peak locations and relative intensities that are unique to the target molecule(s) 100. If the peak locations match the reference peak locations within a predefined margin of error, the target molecule or compound 100 is confirmed to be present in the sample. Similarly, the concentrations of the target molecule(s) 100 can be determined by whether the peak intensities match the reference peak intensities within a predefined margin of error.

In one aspect of the invention, a computing device 134 is provided with a software analysis system 136, which is executed on or by the computing device 134, includes a software routine or executable file for performing multivariate analysis such as principle component analysis (PCA) on the spectra 133 of known and target molecule (e.g., biomolecules, drugs, analytes, or the like). The software analysis system 136 interfaces with a database 138 that contains signature or "fingerprints" of different types of molecules using, for example, PCA signatures. PCA is a post-analysis technique whereby spectral features of known and unknown molecules can be extracted. For example, the spectral features that can be extracted include the peak intensity values at a particular wavelength shifts as well as peak width to height ratios (or other ratios) at particular wavelength shifts. PCA is a statistical analysis technique which reduces the variables in a data set by transforming the data into a new coordinate system. For example, PCA can be used to transform data into a first principal component PC1 and a second principal component PC2 that can be used to extract the most obvious distinctions between data sets. For example, the first principal component PC1 and the second principal component PC2 may be plotted on a new coordinate system whereby each principal component is represented by orthogonal axis. Similar analysis can be done using images obtained with a Raman microscope.

Figure 13B:
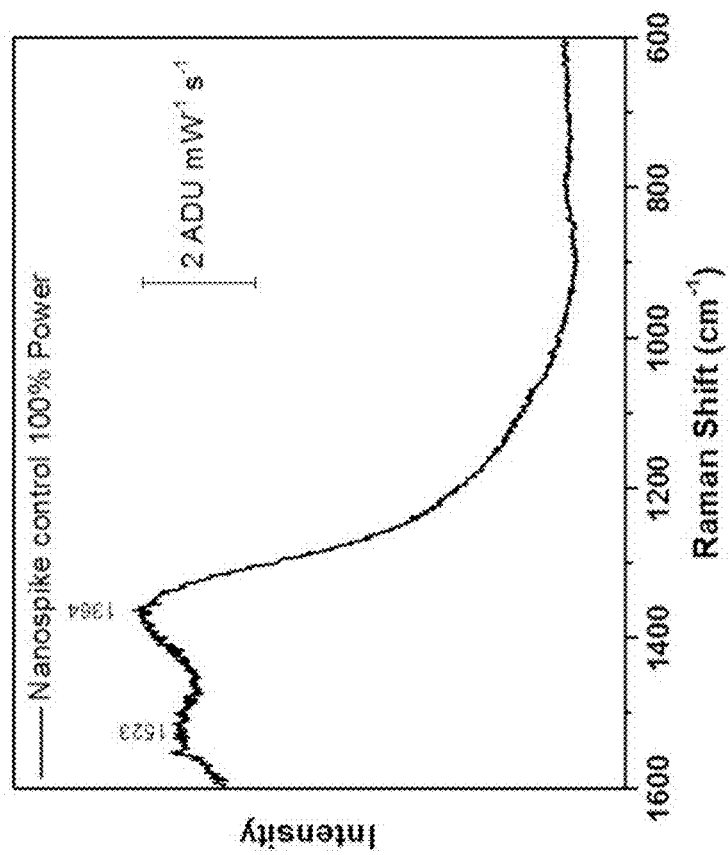
FIG. 13B illustrates the surface-enhanced Raman spectra of the model molecule benzenethiol in the absence of the gold nanostars within a glass microcapillary.
Figure 13A:
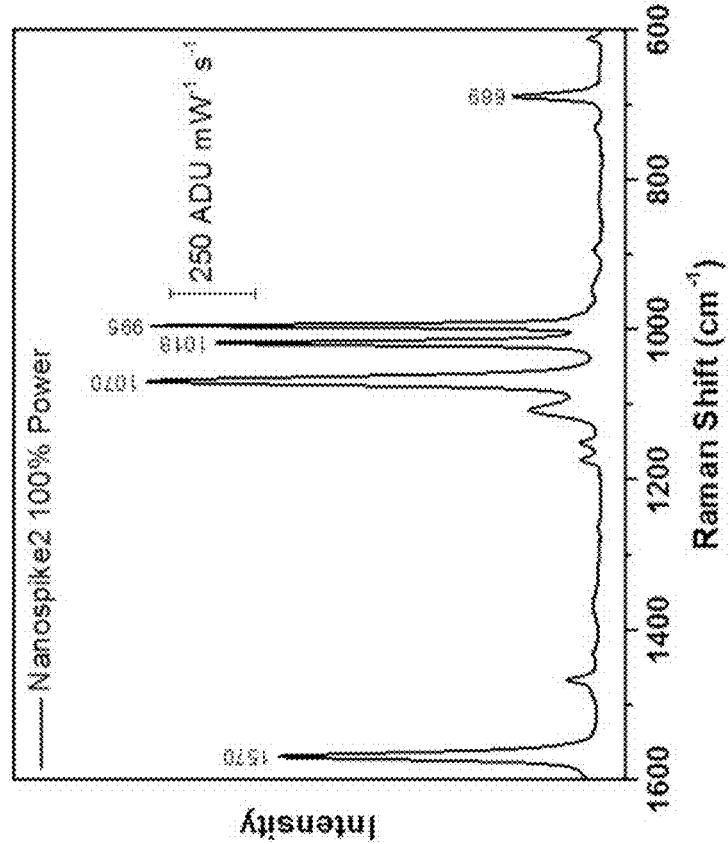
FIG. 13A illustrates surface-enhanced Raman spectra of the model molecule benzenethiol in the presence of the gold nanostars within a glass microcapillary used for the in-situ seed-mediated growth of the nanostructures.
Figure 14:
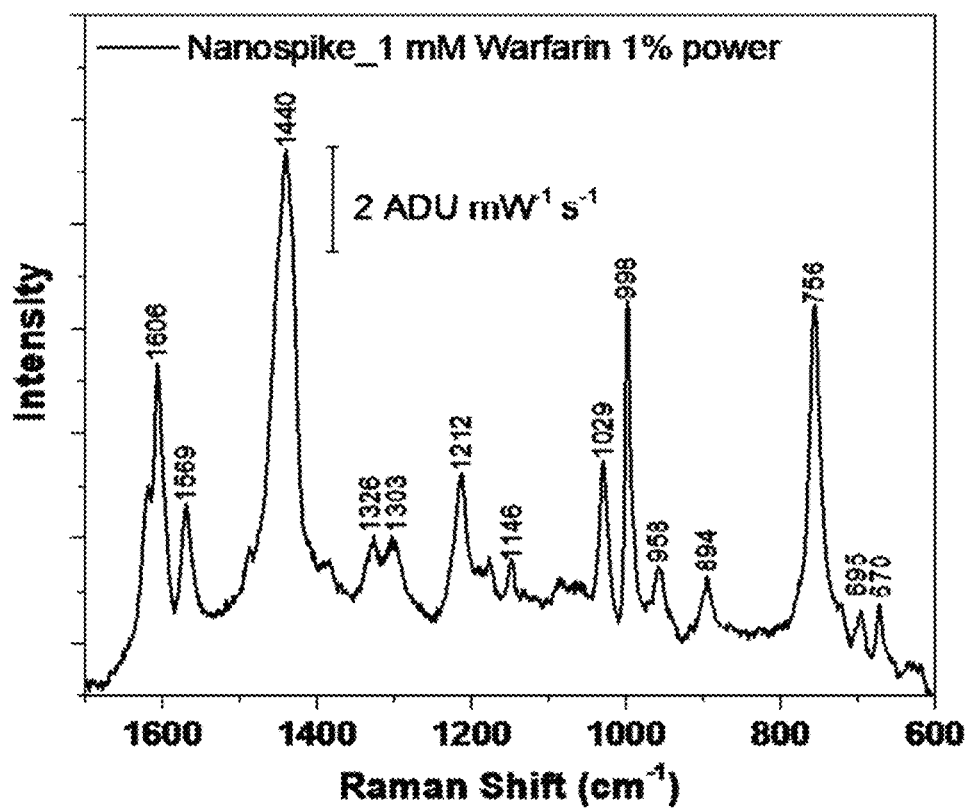
FIG. 14 illustrates surface-enhanced Raman spectra of the molecule Warfarin in the presence of the gold nanostars within a glass microcapillary.

The detection of a target molecule 100, benzenethiol, was successfully demonstrated down to a single monolayer. It was further verified that the detection was not possible using a bare glass surface without nanostars (FIGS. 13A and 13B). Warfarin was also detected using the nanostar platform as seen in FIG. 14. Embodiments for point-of-care devices based on the nanostructured interfaces disclosed herein would include networks or microfluidic channels or capillaries 24 functionalized with in-situ grown plasmonic nanostars 10 that are fabricated via the methods described herein. A portable Raman spectrometer 132 with corresponding SERS reference spectra stored in its memory can be used to measure samples and to determine standard curves for detecting and assessing the concentration of the target molecule or compound 100 in model and/or patient-derived fluids.

While embodiments of the present invention have been shown and described, various modifications may be made without departing from the scope of the present invention. For example, while the systems and methods have largely been described using gold as the metal to form the nanostructures 10, other metallic materials may be used. This includes, for example, silver, although silver may suffer from the limited number of different shapes and morphologies compared to gold and the fact that silver-based nanostructures 10 are more prone to oxidation. Likewise, different metals may be used for the seed particle 23 and the growth solution. For example, core-shell nanostructures 10 may be used with one metal used for the core and another metal used for the shell. In addition, while the preferred embodiments have described the nanostructures 10 being formed on a microfluidic channel or capillary it should be appreciated that the nanostructures 10 may be formed on any fluid-contacting surface 22 of a microfluidic device 24 including, for example, chambers, wells, walls, or other regions of a microfluidic device 24. In addition, while the nanostructures 10 have largely been described as exhibiting plasmonic activity in the NIR wavelength range it should be appreciated that other embodiments may use nanostructures 10 that exhibit plasmonic activity in the visible wavelength range (e.g., about 380 nm to about 780 nm) and ultraviolet range. The invention, therefore, should not be limited, except to the following claims, and their equivalents.

What is claimed is:

1. A microfluidic device for the selective capture and release of cells comprising:
    one or more microfluidic channels or capillaries having one or more inner surfaces functionalized with a plurality of in-situ grown gold anisotropic nanostars disposed thereon, wherein the gold anisotropic nanostars exhibit plasmonic activity in one or more wavelength ranges and further comprise a capture ligands specific to a specific type of cell:
    one or more pumps configured to pump a sample containing the cells through the one or more microfluidic channels or capillaries, wherein at least some of the cells adhere to the capture ligands; and
    a light source configured to deliver a focused beam of light onto the one or more inner surfaces functionalized with the plurality of in-situ grown gold anisotropic nanostars, wherein the focused beam of light is configured to produce localized heating on the gold anisotropic nanostars, which is configured to cause conformation changes in the gold anisotropic nanostars to release the at least some of the cells that adhere to the capture ligands.

2. The microfluidic device of claim 1, wherein one or more of wavelength ranges comprises the near-infrared wavelength range.

3. The microfluidic device of claim 1, wherein the capture ligands comprise an antibody or aptamer.

4. A system comprising the microfluidic device of claim 1, further comprising a Raman spectrometer or Raman microscope configured to obtain Raman spectra or to obtain Raman images of the cells that adhere to the capture ligands.

5. The system of claim 4, wherein the Raman spectra, Raman images, or spectral data is enhanced by the gold anisotropic nanostars disposed on the inner surface of the one or more microfluidic channels or capillaries.

6. The system of claim 4, further comprising a computing device, the computing device containing software executed thereon that identifies the cell type based on the Raman spectra, Raman images obtained by the Raman spectrometer or Raman microscope.

7. A system comprising the microfluidic device of claim 1, further comprising an optical microscope configured to image the cells that adhere to the capture ligands.

8. The system of claim 7, wherein the optical microscope comprises a fluorescent microscope.

9. The system of claim 7, wherein the optical microscope comprises a confocal microscope.

10. The microfluidic device of claim 1, wherein the light source comprises one or more of a laser, light emitting diode (LED), or laser diode.

11. A method of using the microfluidic device of claim 1, comprising pumping the sample through the one or more microfluidic channels or capillaries having one or more cells, wherein one or more of the cells adheres to the gold anisotropic nanostars via the capture ligand.

12. The method of claim 11, further comprising releasing one or more of the adherent cells from the gold anisotropic nanostars by increasing the local temperature with the focused beam of light from the light source directed at one or more target sites on the one or more microfluidic channels or capillaries.

13. The method of claim 12, wherein the focused beam of light is scanned relative to the one or more inner surfaces functionalized with the plurality of in-situ grown gold anisotropic nanostars.

14. The method of claim 12, wherein the focused beam of light is directed at one or more target sites while fluid is pumped through the one or more microfluidic channels or capillaries.

* * * * *